US008354521B2

(12) United States Patent
Li

(10) Patent No.: US 8,354,521 B2
(45) Date of Patent: Jan. 15, 2013

(54) COMPOSITIONS AND METHODS FOR INHIBITING ADIPOGENESIS BY INHIBITION OF CONSTITUTIVE COACTIVATOR OF PPARGAMMA

(75) Inventor: Dechun Li, Fenton, MO (US)

(73) Assignee: Saint Louis University, Saint Louis, MO (US)

( * ) Notice: Subject to any disclaimer, the term of this patent is extended or adjusted under 35 U.S.C. 154(b) by 235 days.

(21) Appl. No.: 12/870,991

(22) Filed: Aug. 30, 2010

(65) Prior Publication Data

US 2011/0014275 A1    Jan. 20, 2011

Related U.S. Application Data

(62) Division of application No. 11/870,736, filed on Oct. 11, 2007, now Pat. No. 7,834,140.

(60) Provisional application No. 60/851,156, filed on Oct. 12, 2006.

(51) Int. Cl.
*C07H 21/04* (2006.01)
*A61K 31/70* (2006.01)

(52) U.S. Cl. .................................. 536/24.5; 514/44

(58) Field of Classification Search .................. None
See application file for complete search history.

(56) References Cited

U.S. PATENT DOCUMENTS

| 5,556,762 A | 9/1996 | Pinilla et al. |
| 2002/0065394 A1 | 5/2002 | Jacobs et al. |
| 2002/0076412 A1 | 6/2002 | Steinman et al. |
| 2008/0318872 A1 | 12/2008 | Xu |

OTHER PUBLICATIONS

Andersen et al., "Evidence of an association between genetic variation of the coactivator PGC-1beta and obesity", Journal of Medical Genetics, 2005, pp. 402-407, vol. 42.
Aranda et al., "Nuclear Hormone Receptors and Gene Expression", Physiological Reviews, 2001, pp. 1269-1304, vol. 81, No. 3.
Auboeuf et al., "Differential recruitment of nuclear receptor coactivators may determine alternative RNA splice site choice target genes", Proceedings of the National Academy of Sciences USA, 2004, pp. 2270-2274, vol. 101, No. 8.
Bannister et al., "The CB co-activator is a histone acetyltransferase", Nature, 1996,pp. 641-643, vol. 384.
Berger et al., "The Mechanisms of Action of PPARs", Annual Review of Medicine, 2002, pp. 409-435, vol. 53.
Castillo et al., "An adipogenic cofactor bound by the differentiation domain of PPAR gamma", The EMBO Journal, 1999, pp. 3676-3687, vol. 18, No. 13.
Chen et al., "Activation of Estrogen Receptor alpha by S118 Phoshorylation Involves a Ligand-Dependent Interaction with TFIIH and Participation of CDK7". Molecular Cell, 2000, pp. 127-137, vol. 6.
Chen et al., "Nuclear Receptor Coactivator ACTR Is a Novel Histone Acetyltransferase and Forms a Multimeric Activation Complex with P/CAF and CBP/p300". Cell, 1997, pp. 569-580, vol. 90.
Corton et al. "Peroxisome Proliferator-Activated Receptor gamma Coactivator 1 in Caloric Restriction and Other Models of Longevity", Journal of Gerontology:Biological Sciences, 2005, pp. 1494-1509, vol. 60A, No. 12.
Cui et al., "The HhH(2)/NDD Domain of the Drosophila Nod Chromokinesin-like Protein Is Required for Binding to Chromosomes in the Oocyte Nucleus", Genetics, 2005, pp. 1823-1835, vol. 171.
Darimont et al., "Structure and specificity of nuclear receptor-coactivator interactions", Genes & Development, 1998, pp. 3343-3345, vol. 12.
Ge et al., "Transcription coactivator TRAP220 is required for PPAR gamma 2-stimulated adipogenesis", Nature, 2002, pp. 563-567, vol. 417.
Glass, "Going nuclear in metabolic and cardiovascular disease", The Journal of Clinical Investigation, 2006, pp. 556-560, vol. 116, No. 3.
Hager et al., "Dynamics of nuclear receptor movement and transcription", Biochimica et Biophysica Acta 1667, 2004, pp. 46-51.
Heery et al., "A signature motif in transcriptional co-activators mediates binding to nuclear receptors", Nature, 1997, pp. 733-736, vol. 387.
Horwitz et al., "Nuclear Receptor Coactivators and Corepressors", Molecular Endocrinology, 1996, pp. 1167-1177, vol. 10.
Ijpenberg et al., "Polarity and Specific Sequence Requirements of Peroxisome Proliferator-activated Receptor (PPAR)/Retinoid X Receptor Heterodimer Binding to DNA", The Journal of Biological Chemistry, 1997, pp. 20108-20117, vol. 272, No. 32.
Jung et al., "Proteomic Analysis of Steady-State Nuclear Hormone Receptor Coactivator Complexes", Molecular Endocrinology, 2005, pp. 2451-2465, vol. 19, No. 10.
Kersten et al., "Roles of PPARs in health and disease", Nature, 2000, pp. 421-424, vol. 405.
Kliewer et al., "Retinoid X receptor interacts with nuclear receptors in retinoic acid, thyroid hormone and vitamin D3 signaling", Nature, 1992, vol. 355.
Kumar et al., "Coregulators and Chromatin Remodeling in Transcriptional Control", Molecular Carcinogenesis, 2004, pp. 221-230; vol. 41. Lee et al., "Transcriptional coregulators of the nuclear receptor superfamily: coactivators and corepressors", Cellular and Molecular Life Sciences, 2001, pp. 289-297, vol. 58.
Li et al., "Constitutive Coactivator of Peroxisome Proliferator-Activated Receptor (PPAR gamma), a Novel Coactivator of PPAR gamma that Promotes Adipogenesis", Molecular Endocrinology, 2007, pp. 2320-2333, vol. 21, No. 10.
Li et al., "EPA and DHA reduce LPS-induced inflammation responses in HK-2 cells: Evidence for a PPAR-gammadependent mechanism", Kidney International, 2005, pp. 867-874, vol. 67.
Lin et al., "Metabolic control through the PGC-1 family of transcription coactivators", Cell Metabolism, 2005, pp. 361-370, vol. 1.

(Continued)

*Primary Examiner* — Tracy Vivlemore
(74) *Attorney, Agent, or Firm* — Randolph Bretton; The Law Office of Randolph Bretton

(57) ABSTRACT

This invention relates generally to compositions and methods which utilization nuclear receptors for regulating adipogenesis in cells. Specifically, the invention is directed to compositions which regulate transcription factor PPARγ, and enhance or inhibit the transcription of genes responsible for directing cell differentiation towards a pathway of adipogenesis. More specifically, disclosed herein is a novel polypeptide coactivator of PPARγ, and fragments thereof, which possess coactivator or corepressor activity. Also related are nucleotide sequences which express these polypeptides. Also disclosed is an interfering RNA that may be used to inhibit adipogenesis.

20 Claims, 20 Drawing Sheets
(4 of 20 Drawing Sheet(s) Filed in Color)

OTHER PUBLICATIONS

Liu et al., "p62, A TFIIH Subunit, Directly Interacts with Thyroid Hormone Receptor and Enhances T3-Mediated Transcription", Molecular Endocrinology, 2005, pp. 879-884, vol. 19, No. 4.

Lonard et al., "Expanding functional diversity of the coactivators", Trends in Biochemical Sciences, 2005, pp. 126-132, vol. 30, No. 3.

Lonard et al., "The Expanding Cosmos of Nuclear Receptor Coactivators", Cell, 2006, pp. 411-414, vol. 125.

Lowell et al., "Brown Adipose Tissue beta 3-Adrenergic Receptors, and Obesity", Annual Review of Medicine, 1997, pp. 307-316, vol. 48.

McInerney et al., "Determinants of coactivator LXXLL motif specificity in nuclear receptor transcriptional activation", Genes & Development, 1998, pp. 3357-3368, vol. 12.

McKenna et al., "Combinatorial Control of Gene Expression by Nuclear Receptors and Coregulators", Cell, 2002, pp. 465-474, vol. 108.

Monsalve et al., "Direct Coupling of Transcription and mRNA Processing through the Thermogenic Coactivator PGC-1", Molecular Cell, 2000, pp. 307-316, vol. 6.

Novac et al., "Nuclear Receptors: Overview and Classification", Current Drug Targets—Inflammation & Allergy, 2004, pp. 335-346, vol. 3.

Omalley, "Sequentiality and processivity of nuclear receptor coregulators in regulation of target gene expression", Nuclear Receptor Signaling, 2003, 3 pages.

Park et al., "A dominant negative PPAR gamma mutant shows altered cofactor recruitment and inhibits adipogenesis in 3T3-L1 cells", Diabetologia, 2003, pp. 365-377, vol. 46.

Puigserver et al., "A Col-Inducible Coactivator of Nuclear Receptors Linked to Adaptive Thermogenesis", Cell, 1998, pp. 829-839, vol. 92.

Puigserver et al., "Activation of PPAR gamma Coactivator-1 Through Transcription Factor Docking", Science, 1999, pp. 1368-1371.

Puigserver et al., "Peroxisome Proliferator-Activated Receptor-gamma Coactivator 1 alpha (PGC-1 alpha): Transcriptional Coactivator and Metabolic Regulator", Endocrine Reviews, 2003, pp. 78-90, vol. 24, No. 1.

Puigserver, "Tissue-specific regulation of metabolic pathways through the transcriptional coactivator PGC1-alpha", International Journal of Obesity, 2005, pp. S5-S9, vol. 29.

Qi et al., "Transcriptional Coactivator PRIP, the Peroxisome Proliferator-activated Receptor gamma (PPAR gamma)-interacting protein, Is Required for AR gamma-mediated Adipogenesis", The Journal of Biological Chemistry, 2003, pp. 25281-25284, vol. 278, No. 28.

Robyr et al., "Nuclear Hormone Receptor Coregulators in Action: Diversity for Shared Tasks", Molecular Endocrinology, 2000, pp. 329-347.

Rosen et al., "Transcriptional regulation of adipogenesis", Genes & Development, 2000, pp. 1293-1307, vol. 14.

Rosen et al., "PPAR gamma: a Nuclear Regulator of Metabolism, Differentiation, and Cell Growth", The Journal of Biological Chemistry, 2001, pp. 37731-37734, vol. 276, No. 41.

Sancar et al., "Molecular Mechanisms of Mammalian DNA Repair and the DNA Damage Checkpoints", Annual Review of Biochemistry, 2004, pp. 39-85, vol. 73.

Shibata et al., "Role of Co-activators and Co-repressors in the Mechanism of Steroid/Thyroid Receptor Action", Recent Progress in Hormone Research, 1997, pp. 141-164, vol. 52.

Smith et al., "Coregulator Function: A Key to Understanding Tissue Specificity of Selective Receptor Modulators", Endocrine Reviews, 2004, pp. 45-71, vol. 25, No. 1.

Spencer et al., "Steroid receptor coactivator-1 is a histone acetyltransferase", Nature, 1997, pp. 194-198, vol. 389.

Spiegelman et al., "Biological Control Through Regulated Transcriptional Coactivators", Cell, 2004, pp. 157-167, vol. 119.

Tchereanova et al., "Modulation of Estrogen Receptor-alpha Transcriptional Activity by the Coactivator PGC-1*", The Journal of Biological Chemistry, 2000, pp. 16302-16308, vol. 275, No. 21.

Teng et al., "FIZZ1/RELMalha, a Novel Hypoxia-Induced Mitogenic Factor in Lung with Vasoconstrictive and Angiogenic Properties", Circulation Research, 2003, pp. 1065-1067, vol. 92.

Tong et al., "Hypoxia-Induced Mitogenic Factor Modulates Surfactant Protein B and C Expression in Mouse Lung", American Journal of Respiratory Cell and Molecular Biology, 2006, pp. 28-38, vol. 34.

Tontonoz et al., "Stimulation of Adipogenesis in Fibroblasts by PPAR gamma 2, a Lipid-Activated Transcription Factor", Cell, 1994, pp. 1147-1156, vol. 79.

Tsodikov et al., "Crystal structure and DNA binding functions of ERCC1, a subunit of the DNA structure-specific endonuclease XPF-ERCC1", Proceeding of the National Academy Sciences USA, 2005, pp. 11236-11241, vol. 102, No. 32.

Uldry et al., "Complementary action of the PGC-1 coactivators in mitochondrial biogenesis and brown fat differentiation", Cell Metabolism, 2006, pp. 333-341, vol. 3.

Verma et al., "The Ubiquitin-Conjugating Enzyme UBCH7 Acts as a coactivator for Steroid Hormone Receptors", Molecular and Cellular Biology, 2004, pp. 8716-8726, vol. 24, No. 19.

Wang et al., "Critical roles of the p160 transcriptional coactivators p/CIP and SRC-1 in energy balance", Cell Metabolism, 2006, pp. 111-122, vol. 3.

Wolins et al., "OP9 mouse stromal cells rapidly differentiate into adipocytes: characterization of a useful mew model of adipogenesis", Journal of Lipid Research, 2006, pp. 450-460, vol. 47.

Zhu et al., "Cloning and Identification of Mouse Steroid Receptor Coactivator-1 (mSRC-1), as a Coactivator of Peroxisome Proliferator-Activated Receptor gamma", Gene Expression, 1996, pp. 185-195, vol. 6.

Zhu et al., "Isolation and Characterization of Peroxisome Proliferator-activated Receptor (PPAR) Interaction Protein (PRIP) as a Coactivator for PPAR*", The Journal of Biological Chemistry, 2000, pp. 13510-13516, vol. 275, No. 18.

Zhu et al., "Isolation and Characterization of PBP, a Protein That Interacts with Peroxisome Proliferation-activated Receptor*", The Journal of Biological Chemistry, 1997, pp. 25500-25506, vol. 272, No. 41.

```
human   ----------------------------------------------------------------MGVRGLQGFVGSTCPHICTVVNFKELAEHHRS  32
mouse   ----------------------------------------------------------------MGVRGLQGFVGSTCPHICTIVNIHELAERHRN  32
rat     -----------------------------------------------------------------------MVLKAFA---THQKVCFTVNLHELAESHRA  27
dog     ----------------------------------------------------------------MGVRGLQGFVGSTCPHICTVVNFKELAEHHRN  32
cattle  MAESVGGRGGRLEPAHLRASLRAWRLGPQAPHGRGRSRSPFTAEKESDSRWILPRSSIMGVRGLHGFVASSCPHVCTVVNFKELAERHRS  90 human   KYPGCTPTIVVDAMCCLRYWYTPESWICGGQWREYFSALRDFVKTFTAAGIKLIFFFDGMVEQDKRDEWVKRRLKNNREISRIFHYIKSH 122
mouse   KYPGCTPTIVVDAMCCLRYWYTAESWVCGGQWREYYCALRNFVAAFTSAGIKLIFFFDGMVEPGKRDEWVKRRLKNNREISKIFHYIKSL 122
rat     KYPGSTPTIVVDAMCCLRYWYTAESWVCGGQWREYYSALRDFLAAFTSAGIKLIFFFDGTVEPGKRDEWVKRRLKNNREISRIFHYIKSK 117
dog     QHPGCTPTIVVDAMCCLRYWYTPESWICGGQWREYFSSLRDFVKTFTTTVGIKLIFFFDGMVEQEKRDEWVKRRLKNNREISRIFHYIKSH 122
cattle  QHPGGTPTIVVDAMCCLRYWYTPESWVCGGQWREYYSSLREFVRTFTAVGIKLIFFFDGMVEQSKRDEWVKRRLKNNREIAKIFHYIKSR 180 human   KEQPGRNMFFIPSGLAVFTRFALKTLGQETLCSLQEADYEVASYGLQHNCLGILGEDTDYLIYDTCPYFSISELCLESLDTVMLCREKLC 212
mouse   RDQPGRNMFFIPSGLAIFTRFALKTLGQETFCSLQEADYEVASYGLQHNCLGILGEDTDYLIYDTCPYFSIGDLCLESLQTIMLCREKLC 212
rat     REQPGRNMFFIPSGLAIFTRFALKSLGQETFCSLQEADYEVASYGLQHNCLGILGEDTDYLIYDTCPYLSIGDLCLESLQTILLCREKLC 207
dog     KEQPGRNMFFIPSGLAIFTRFALKALGQETLCSLQEADYEVASYGFQNNCLGILGEDTDYLIYDTCPYFSIGDLCLESLSTVMLCRKKLC 212
cattle  REQPGRNMFFIPSGLAIFTRFALKALGQETLCSLQEADYEVASYGFQNNCLGILGEDTDYLIYDTCPYFSISELSLDSLDTVMLCREKLC 270 human   ESLGLCVADLPLLACLLGNDIIPEGMFESFRYKCLSSYTSVKENFDKKGNIILAVSDHISKVLYLYQGEKKLEEILPLGPNKALFYKGMA 302
mouse   ESLGLRVADLPLLACLLGNDITPESMFESFRYKCLSSYASVKENAGKKGNIILAVSDYISKVLHLYQGEKKIEEMLPLGPNKALFYKGVT 302
rat     ESLGLRVSDLPLLACLLGNDIIPEGMFESFRYKCLSSYASVKENAGKKGNIILAVSDYISKVLHLYQGEKKIEEMLPLGPNKALFYKGVT 297
dog     ESLNINVADLPLLACLLGNDIIPEGMFESFRYKCLSSYTSVKENFDKKGNILAVADHISKVLHSHQGEKKLEDMLPLGPNKALFYKGVA 302
cattle  QSLGLHLADLPLLACLLGNDVIPEGMFESFRYKCLTSYASVRESCDRKGNVILAVAEHISKVLRLHQGEKKLEEMLPLGPNKALFYKGVA 360 human   SYLLPGQKSPWFFQKPKGVITLDKQVISTSSDAESREEVPMCSDAESRQEVPMCTGPESRREVPVYTDSEPRQEVPMCSDPEPRQEVPTC 392
mouse   SYLLPGQKSPWLVQKPKGMITDKQQMVSLN------------------------PESK------------QEVPMCIDPEFKQEVPVC 354
rat     SYLLPGQKSPWLVQKPKSIITDK-QMASLN------------------------PGSK------------QEVPMCIDPEFKQEVPVC 348
dog     SYLLPGQKSPWFFQKPKSLISLGKQVVSMN------------------------PESK------------QEVPMCTEPESKQEVPMC 354
cattle  SYLLPGQKSPWFIQKPEDVVTLDKQVLSMSSD-----------------------PESK------------QEFPVCMDSESKQKLPVG 414 human   TGPESRREVPMCSDPEPRQEVPMCTGPEARQEVPMYTDSEPRQEVPMTDSEPRQEVPMYTGSEPRQEVPMTGPESRQEVPMYTGPESR 482
mouse   TNPESMQEVPMCMCDPEPNQEASMCTDPESKQEVPMCTD-------------------------------------SESKPEVSQYTNPESK 408
rat     TNPESMQEVPMCMCDPEPNQEASVCMDPESKPEVPMCTD-------------------------------------PESKPEVPLYTNPESK 402
dog     TPPESRQGVPMCTDPESRQGVPMCTDPESRQGVPMCTD-------------------------------------PESRQGVSMCTDPESK 408
cattle  TDPEFNLEAPMCTNTEVKQEDPVNVGPEAKHQVTVVLD----------------------------------------PEILKVGGHAHPNTT 467 human   QEVLIRTDPESRQEIMCTGHESKQEVPICTDPISKQEDSMCTHAEINQKLPVATDFEFKLEALMCTNPEIKQEDPTNVGPEVKQQVTMVS 572
mouse   Q--------------------------------------------KLPSGIDTEFNLEALMCTHPEFKQEDVMDMEPEIK-QVTMVS 450
rat     Q--------------------------------------------KSPSEIDPKCNLEALTCTYPEVKQEDAMDMEPEIK-QATMVS 444
dog     Q--------------------------------GQKLPPGADPEFKLEALMCTNPAIK-EDLVNMEPEVK-QVTLVS 451
cattle  Q------------------------------------SLDGGLEADLHVEVPTSMQPEEKGEQRQDRGPSLR-LASMLS 509 human   DTEILKV-------------------ARTHHVQAESYLVYNIMSSGEIECSNTLEDELDQALPSQAFIYRPIRQRVYSLLLEDCQDVTS 642
mouse   ESEILKV-------------------ARMHHVHSESYLVYNILSSGEIECSNTLEDELDQALPSQAFIYRPVRQRVYALLLGDWKDGAS 520
rat     ESEILKV-------------------ARMHHVHSESYLVYNILSSGEIECSNTLEDELDQALPSQAFIYRPVRQRVYSLLLEDWKDGAS 514
dog     DPDILKV-------------------ARADHVQAESYLVYNIMSSGEIECSNTLEDALDQALPSQAFVYRPVRQRVYSLLLGDGGDGAG 521
cattle  VTHVHRVSDAIQPSHPLNKLHLIVGQVARAQHVQAESYLVYSVMSSGEVECSNSLEDATDQALPSQAFVYRPVRQRVYSLLLGGGGGGSS 599 human   TCLAVKEWFVYPGNPLRHPDLVRPLQMTIPGGTPSLKILWLNQEPEIQVRRLDTLLACFNLSSSREELQAVESPFQALCCLLIYLFVQVD 732
mouse   TGPVVKEWFVYPGNSLKHPDLVRPLQMTVQGGTPSLEVLWLSQEPAVQAQRLDTLLACFNLSSSREELQAVESPLRALCCLLIYLFVQVD 610
rat     TGPVVKEWFVYPGNSLKHPDLVRPLQMTVQGGTPSLEVLWLSQEPAAQARRLDTLLACFNLSSSREELQSVESPLRALCCLLIYLFVQVD 604
dog     TCPTVKEWFVYSGNPLRHPDLVRPLQMNIPGGTPNLKLLWLNQEEPGTQARRVEALLGCFDLSSSREELQAVENPFRALCCLLTYLFVQVD 611
cattle  TGPAVKEWFVYSGNPLRQPDLVRPLQMNIPGGTPSLRQLWLSQEPGIQAQRLDTLLACFDLSSSREELQAVERPFQALCCLLVYLFVQVK 689 human   TLCLEDLHAFIAQALCLQGKSTSQLVNLQPDYINPRAVQLGSLLVRGLTTLVLVNSACGFPWKTSDFMPWNVFDGKLFHQKYLQSEKGYA 822
mouse   TLSLEDLHAFIAQALCLQGKSTSQLMHLQLDYINSRAVQLGSLLVRGLTTLVLVNSACGFPWTTSEFMPWNVFDGKLFHQKYLQSEKGYA 700
rat     TLSLEDLHAFIAQALCLQGKSTSQLMHLQLDYINSRAVQLGSLLVRGLTTLVLVNSACGFPWTTSDFMPWNVFDGKLFHQKYLQSEKGYG 694
dog     TLCLEDLHAFIAQALCLQGKSTVQLVDLQLDYIDSRAVQLGSLLVRGLTTLVLVNSACGFPWRTSDFMPWNVFDGKLFHQKYLQSEKGYA 701
cattle  ------HKSDLGWEQTAQRRAAFCFARWGQEPRNK-------------CLPAQASEFSPQRRPFMEAPCSPGPALPWRLVRRKR--L 755 human   VEVLLEQNRSRLTKFHNLKAVVCKACMKENRRITGRAHWGSHHAG-RWGRQGSSYHRTGSGYSRSSQGQPWRDQGPGSRQYEHDQWRRY 910
mouse   VEVLLEQNRSWLTKFHNLKAVVCKACSKENRRIVGRTHWDSPYTG-RQGRQGYSSYRTDSTHGHS--GQSWRNQGSGGRQHERNHWRRY 786
rat     VETLLEQNRSWLTTFHNLKAVVCKACSKENRRIVGRIHWNSHYTG-RQGRQGHGSYRSGSTHGHS--GQSWRDQGSGGRQHEHDHWRRY 780
dog     VEALVEHNRSRLTRFHALKSVVCKACAKENRRIVSRQHWRSHQPGGHHGAQARGREVLGPQSLSTAGDEPMTDQGPCFGVA-------- 782
cattle  LDVLL------LGSLLNQTSI---------------------------------------------------------------------- 770
```

COMPOSITIONS AND METHODS FOR INHIBITING ADIPOGENESIS BY INHIBITION OF CONSTITUTIVE COACTIVATOR OF PPARGAMMA

RELATED APPLICATIONS

This patent application is a divisional application of U.S. patent application Ser. No. 11/870,736 filed Oct. 11, 2007, now U.S. Pat. No. 7,834,140, allowed, which claims priority from U.S. provisional patent application Ser. No. 60/851,156, filed Oct. 12, 2006. The above documents are incorporated herein by reference in their entirety.

GOVERNMENT SUPPORT CLAUSE

This work was supported by the National Institutes of Health Grant Number HL075755. The U.S. Government has certain rights in this invention.

BACKGROUND OF THE INVENTION

1. Field of the Invention

This invention relates generally to compositions and methods of regulating adipogenesis in cells. Specifically, the invention is directed to the utilization of nuclear receptors and their cofactors including PPARγ. Also related are polypeptides that enhance or inhibit PPARγ activation and the subsequently the transcription of genes responsible for adipogenesis. Also related are nucleotide sequences which express these polypeptides.

2. Description of the Related Art

Obesity, defined as a state of pathologically excessive adipose tissue mass, has been identified as an epidemic in the U.S. for more than two decades. Yet the numbers of overweight and obese adults and children continues to rise. Currently, the rates of both overweight and obesity in the U.S. are 61 percent and 14 percent in adults and children, respectively. Among U.S. adults aged 20-74 years, the prevalence of overweight (defined as BMI 25.0-29.9) has increased from 33 percent in 1980 to 35 percent of the population in 1999. The disease is associated with several serious health conditions including type 2 diabetes mellitus, heart disease, high blood pressure and stroke. It is also linked to higher rates of certain types of cancer. Obesity is an independent risk factor for heart disease, hypoxia, sleep apnea, hernia, and arthritis. Obesity is the seventh leading cause of death in the U.S. The total cost of obesity and related conditions by some estimates is $100 billion annually.

The development of obesity requires the continuous differentiation of new adipocytes throughout life, and this process of adipocyte differentiation from preadipocytes is called adipogenesis. Many studies have demonstrated the importance of transcription factors, especially nuclear receptors (NRs) and their coactivators, in adipocyte proliferation, gene expression regulation, and differentiation.

Nuclear receptors are a superfamily of transcription factors (TFs) that regulate the expression of target genes in response to steroid hormones and other ligands. To date, there are 48 NRs reported and each plays distinct or interrelated functions (Ruan et al. (2005) Kidney International 68, 2444-2461). However, recent studies have demonstrated that NR functions are modulated by a large group of proteins called coregulators. These coregulators include coactivators which promote transcription and corepressors which attenuate promoter activity when recruited into the promoter regions of specific genes (McKenna and O'Malley (2002) Endocrinology 143, 2461-2465; Glass (2006) J. Clin. Invest. 116, 556-560; Aranda and Pascual (2001) Physiol. Rev. 81, 1269-1304; McKenna and O'Malley (2002) Cell 108, 465-474; Smith and O'Malley (2004) Endocr Rev 25, 45-71; Darimont et al. (1998) Genes Dev. 12, 3343-3356; Xu (2005) Biochem Cell Biol 83, 418-428; O'Malley (2003) Nucl Recept Signal 1, e010; Lee et al. (2001) Cell Mol Life Sci 58, 289-297; Robyr et al. (2000) Molecular Endocrinology 14, 329-347).

Regulation of adipogenesis is central to conditions of overweight and underweight. Adipogenesis is a multistage process that includes expression of a complex set of transcription factors that initiate transcription of preadipocyte- or adipocyte-specific genes. This transcriptional cascade includes expression of key adipogenesis regulators, such as PPARs, CCAAT/enhancer binding protein (C/EBP), and the basic helix-loop-helix (bHLH) family of transcription factors such as ADD1/SREBP1c (Rosen et al. (2000) Genes Dev. 14, 1293-1307). These transcription factors activate genes encoding enzymes that are involved in lipid storage and transport such as adipocyte-specific fatty acid binding protein (aP2) and perilipin, and genes encoding secreted proteins or adipokines that modulate preadipocyte and adipocyte functions such as adiponectin and leptin. In adipocytes, PPARγ regulates the expression of genes involved in lipid synthesis, storage, and transportation (Berger and Moller (2002) Annu Rev Med 53, 409-435). PPARγ is essential to activate the promoters of acyl-CoA oxidase and aP2 and many other fat-cell specific genes (Kliewer et al. (1992) Nature 355, 446-449; Tontonoz et al. (1994) Cell 79, 1147-1156).

Coactivators play critical roles in this nuclear receptor directed adipogenesis program. The importance of coactivators in metabolism and adipogenesis are well documented (Castillo et al. (1999) EMBO J 18, 3676-3687; Puigserver et al. (1998) Cell 92, 829-839; Puigserver and Spiegelman (2003) Endocrine Rev 24, 78-90; Qi et al. (2003) J. Biol. Chem. 278, 25281-25284; Ge et al. (2002) Nature 417, 563-567; Andersen et al. (2005) J Med Genet 42, 402-407; Wang et al. (2006) Cell Metabolism 3, 111-122). Most coactivators identified to date interact with PPARγ through its C-terminal AF-2 domain or LBD domain, which is dependent on or enhanced by ligand binding, and mediated by the signature cofactor motif, LXXLL, (McInerney et al. (1998) Genes Dev. 12, 3357-3368). For example, coactivators SRC-1/NCoA-1, CBP/p300, pCAF, and TRAP220 interact with the LBD domain of PPARγ (Robyr et al. (2000) Molecular Endocrinology 14, 329-347; Castillo et al. (1999) EMBO J 18, 3676-3687; Nolte et al. (1998) Nature 395, 137-143; Zhu et al. (2000) J. Biol. Chem. 275, 13510-13516). Other coactivators such as PGC-1α interact with PPARγ through the PPARγ DNA-binding and hinge domains (Puigserver et al. (1998) Cell 92, 829-839). PGC-2 binds to the PPARγNB domain, which is independent of ligand and LXXLL motif binding. Many NR coactivators such as members of p160/SRC and PGC-1 family are highly versatile. They are expressed in a variety of tissues and coactivate a wide spectrum of NRs including PPARγ (McKenna & O'Malley (2002) Cell 108, 465-474; Puigserver et al. (1998) Cell 92, 829-839; and Lin et al. (2005) Cell Metab 1, 361-370). For example, PGC-1α is also a coactivator for estrogen receptor (ER)α. Multiple sites in PGC-1α govern its interaction with ERα, but the presence of an LXXLL motif is required for PGC-1α's ligand-dependent binding to ERα (Tcherepanova et al. (2000) J. Biol. Chem. 275, 16302-16308). Therefore, whether a ligand is required for the NR-coactivator interaction mainly depends upon whether LBD domain of NR is involved in the interaction.

Modulation of nuclear receptors, their cofactors, and their pathways will offer new avenues for therapeutic strategies to combat obesity and diseases associated with an overweight as well as underweight conditions. Therefore, the inventor has sought to address the issue of adipogenesis, through the use of the novel nuclear receptor coactivator and its ability to promote or inhibit transcription.

SUMMARY OF THE INVENTION

The present invention relates to novel polypeptides with act as cofactors for the nuclear transcription factor PPARγ. The inventor has designated these polypeptides, Constitutive Coactivator of PPARgamma (CCPG). These polypeptides and fragments of these polypeptides act as coactivators and corepressors of PPARγ and thereby modulate PPARγ adipocyte specific gene expression.

The invention also relates to isolated nucleotide sequences, which express CCPG polypeptides and CCPG fragments with PPARγ transcriptional activating or inhibiting activity.

The invention also relates to interference RNA capable of specifically inhibiting translation of a CCPG polypeptide in a cell.

The invention also relates to nucleotide sequences encoding CCPG polypeptides, further incorporated into expression vectors or nucleotide delivery systems.

Therefore, the invention relates to a composition capable of effecting adipogenesis by modulating PPARγ activation and adipocyte specific gene expression.

It is envisioned that the instant invention may be used in vitro for the study of adipogenesis, obesity or related conditions, and/or may be administered in vivo for the treatment of uncontrolled adipogenesis, obesity or related conditions.

REFERENCE TO COLOR FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention relates to compositions and methods useful in regulating adipogenesis in cells. Specifically, the present invention relates to nucleotide sequences of mouse and (SEQ ID NO:6) human (SEQ ID NO:7), as well as rat (SEQ ID NO:8), canine (SEQ ID NO:9), and bovine (SEQ ID NO:10) which encode a CCPG. CCPG polypeptides which when present in the nucleus of a cell, function as PPARγ coactivators. Also encoded by these nucleotide sequences are polypeptide fragments of CCPG, at least one of which has been shown to coactivate PPARγ and at least one of which has been shown to inhibit PPARγ activation. These nucleotide sequences, when expressed in a mammalian cell will enhance or inhibit PPARγ activity and the subsequently the transcription of adipogenic specific genes. Disclosed are CCPG polypeptide fragments, and related nucleotide sequences that activate or inhibit PPARγ. The present invention also relates to nucleotides sequences for interference RNA (RNAi), (SEQ ID NO:11, SEQ ID NO:12) which may be expressed in a cell to inhibit translation of endogenous CCPG, thereby reducing the amounts of CCPG available to activate PPARγ, and reducing transcription of adipogenic specific genes. The present invention also relates to methods that may be used to introduce a nucleotide sequences encoding a CCPG or a CCPG RNAi into mammalian cells.

PPARgamma

Peroxisome proliferators activated receptor gamma (PPARγ) is a principal transcription factor in the determination of adipogenesis. It is known to require interaction with several coregulators before it will initiate transcription of adipogenic genes. Initiation of gene transcription requires the binding of a ligand to PPARγ. Normal ligands for PPARγ are free fatty acids (FFAs) and eicosanoids. PPARγ forms a heterodimer with RXRα, and further binds to the specific peroxisome proliferator response elements (PPREs) of DNA to initiate gene transcription. This event requires recruitment of several additional transcriptional coactivators including p62, p44, cdk7, XPD and possibly others (Rosen and Spiegelman (2001) J. Biol. Chem. 276, 37731-37734).

Constitutive Coactivator of PPARgamma (CCPG)

Figure 1:
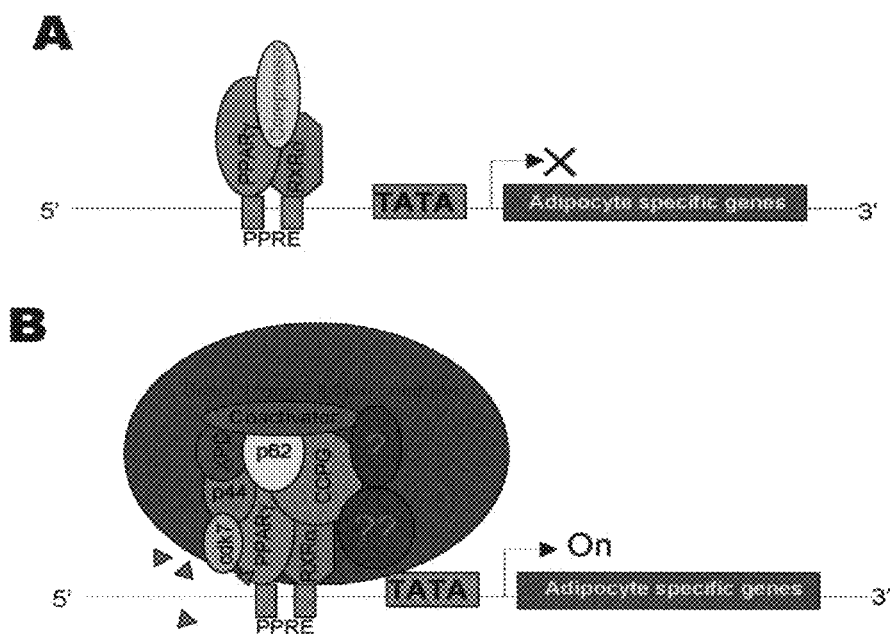
FIG. 1 illustrates the proposed mechanism of CCPG in adipocyte specific gene expression. (A) Corepressors bind to PPARγ and RXRα, preventing further interaction with coactivators and gene transcription. (B) CCPG binds to PPARγ and RXRα, displacing corepressors and allows recruitment of coregulators p62, p44, cdk7, XPD and possibly other coactivators. Adipocyte specific gene transcription and adipogenesis is then initiated.

The present invention relates to a polypeptide coactivator, designated Constitutive Coactivator of PPARgamma or CCPG. CCPG binds and activates PPARγ independent of ligand binding. As illustrated in FIG. 1 and in the examples below, CCPG regulates activation of PPARγ and subsequently the transcription of genes leading to adipogenesis. While not agreeing to be bound by theory, CCPG binds to elements of the basal transcription complex, PPARγ and RXRα (FIG. 1A). This binding displaces corepressor molecules associated with PPARγ and RXRα, and allows the recruitment of coregulators p62, p44, cdk7, XPD and possibly other coregulators (FIG. 1B).

The inventor has cloned a nucleotide sequence, which expresses a mouse CCPG. Through a Genbank search the inventor found this sequence to be homologous with a nucleotide sequence (DQ873694), which encodes an uncharacterized mouse KIAA1838-like protein (NM_024203). Also through Genbank the inventor identified a nucleotide sequence associated with human chromosome 6, (NW_923184) for which no polypeptide was known. The inventor cloned this human nucleotide sequence (DQ873695) and discovered that it expresses a human CCPG polypeptide (ABH09086). Subsequently, through Genbank, using the mouse CCPG polypeptide sequence as a reference, the inventor further identified previously uncharacterized polypeptides with close homology to mouse CCPG, which the inventor designated rat (XP_218006), canine (XP_855466), and bovine (XP_602628) CCPG (Table 1).

Disclosed are polypeptide sequences of the Constitutive Coactivator of PPARγ (CCPG) of mouse (SEQ ID NO:1), human (SEQ ID NO:2), rat (SEQ ID NO:3), canine (SEQ ID NO:4), and bovine (SEQ ID NO:5). These CCPG polypeptides or fragments of these CCPG polypeptides will modulate the activation of transcription factor PPARγ and subsequently transcription of adipogenic genes. Also disclosed are nucleotide sequences encoding mouse (SEQ ID NO:6), human (SEQ ID NO:7), rat (SEQ ID NO:8), canine (SEQ ID NO:9), and bovine (SEQ ID NO:10) CCPG polypeptides or fragments of CCPG polypeptides.

Nucleotide sequences encoding CCPG polypeptides or fragments thereof when introduced into the nucleus of a mammalian cell, will express a CCPG which will modulate the activation of transcription factor PPARγ and the subsequent transcription of adipogenic genes. Therefore, one embodiment of the present invention is directed to isolated human nucleotide sequence encoding a CCPG polypeptide or fragment of a human CCPG polypeptide with PPARγ activator or repressor activity. Another embodiment is directed to nucleotide sequences encoding fragments of mouse CCPG polypeptides with PPARγ activator or repressor activity. These nucleotide sequences when expressed in a mammal cell provide CCPG polypeptides, or fragments of CCPG polypeptides, which localize to the nucleolus and either, enhance or inhibit the adipogenic transcriptional activity of PPARγ.

As demonstrated in the examples, a nucleotide sequence of SEQ ID NO:6, when expressed in a cell, will provide expression of the full length CCPG polypeptide set forth in SEQ ID NO: 1. This polypeptide will function as a coactivator of PPARγ thereby initiating transcription of adipogenic specific genes in mammalian cells.

Similarly, also demonstrated in the examples, an isolated nucleotide sequence encoding amino acid residues 1-561 of SEQ ID NO:1, when expressed in a cell, will provide a polypeptide fragment of CCPG. This polypeptide will also function as a coactivator of PPARγ and will initiate transcription of adipogenic specific genes.

Alternatively, a nucleotide encoding amino acid residues 562-786 of SEQ ID NO:1, when expressed in a cell, will provide a polypeptide with PPARγ corepressor properties, thereby inhibiting PPARγ activation. CCPG has multiple sites of contact with PPARγ and therefore possibly multiple regions with activating or inhibitory activity. One of ordinary skill in the art will appreciate that by encoding shorter polypeptide fragments of CCPG and expressing them in a cell, one would be likely to identify polypeptides of fewer residues that possess the PPARγ activating properties of the CCPG coactivating polypeptide (1-561 SEQ ID NO:1), or, alternatively, the inhibitory properties of the CCPG corepressor polypeptide (562-786 SEQ ID NO:1). One of ordinary skill in the art will also appreciate that various mutations or derivations of this polypeptide sequence, including amino acid substitutions, insertions, or modifications, may also result in a CCPG polypeptide with increased or decreased PPARγ activating capacity. The inventor has identified a method of rapidly screening and identifying polypeptides or compounds with for PPARγ regulatory activity (Example 7). The inventor also provides an antibody that may be useful to identify or localize a CCPG polypeptide, for example in western blots, or immunocyte chemistry (Example 1).

Figure 2:
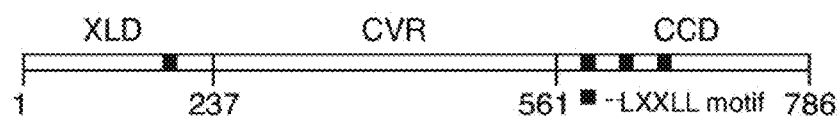
FIG. 2 illustrates the cloning and alignment of CCPG sequences. (A) Alignment of mouse (SEQ ID NO:1), human (SEQ ID NO:2), rat (SEQ ID NO:3), dog (SEQ ID NO:4), and bovine (SEQ ID NO:5) CCPG amino acid sequences. Shaded areas represent conserved amino acids among species. LXXLL motifs are underlined. (B) Schematic representation of the structure of mouse CCPG. CCPG consists of an N-terminal XPG-like domain (XPD), a central viable hinge region (CVR) and a C-terminal conserved domain (CCD). Putative and characteristic domains are marked with numbers. (C) Western blot analysis of recombinant mouse CCPG with anti-CCPG polyclonal antibody. HEK-293 cells were transfected with plasmid pcDNA3-CCPG (lane 1) and pcDNA3 empty vector (lane 2) or without transfection (lane 3). The arrow indicates the recombinant CCPG expressed as a ~95 kD protein.
Figure 2:
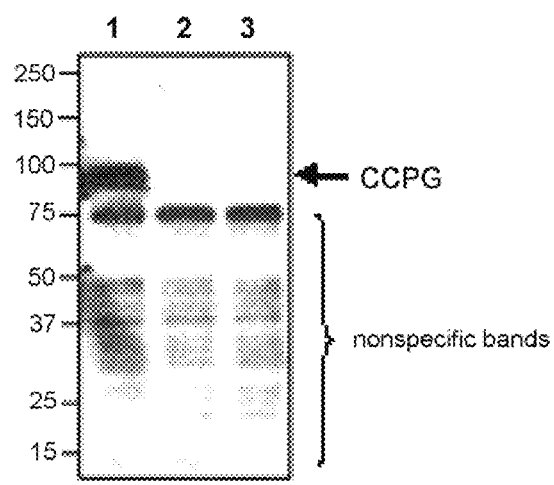

Then inventor has identified and cloned CCPG from mouse and human, and by sequence comparison in Genbank has identified homologs in rat, canine, and bovine. These amino acid sequences from mouse, human, rat, canine, and bovine share from 92 to 67 percent identity (Table 1). Regions of varying sequence identify are dispersed though out the CCPG polypeptides of mouse, human, rat, dog, and cattle (FIG. 2A). It is well known that amino acid sequences, which are highly conserved between species, are also likely to be functional across different species, whereas non-conserved amino acid sequences may often be substituted without a loss of activity. It is also known that polypeptide fragments with conserved amino acid sequences are likely to possess the various functional activities of the intact polypeptide. The inventor has determined amino acid sequence identity is more closely conserved in specific regions of the CCPG polypeptide. For example, amino acid residues 1-320 of mouse and human CCPG are conserved at 87 percent identity (Table 2). Similarly, amino acid residues 420-786 of mouse and human CCPG are conserved at 80 percent identity. A CCPG polypeptide, or fragment thereof, which incorporates these or other conserved amino acid is likely to possess PPARγ activation or repression properties, and, is also likely to exhibit these properties in mice, humans or other mammals. Therefore, another embodiment is an isolated nucleotide sequence which expresses a polypeptide with sequence identity to SEQ ID NO:1 or SEQ ID NO:2 or fragments thereof. By way of example, an isolated nucleotide sequence which encodes a polypeptide with 99 percent, 95 percent, 90 percent, 85 percent, 80 percent, 75 percent, 70 percent, and 68 percent identity with SEQ ID NO:1 or SEQ ID NO:2 or fragments thereof.

These CCPG polypeptides or fragments of CCPG polypeptides, encoded by isolated nucleotide sequences, maybe further incorporated into expression vectors, and/or delivery systems including viral delivery systems and transfected into cells where they may be expressed so as to regulate PPARγ activation and subsequently adipogenesis. In addition, these nucleotide sequences, amino acid sequences, and antibodies are invaluable tools in the study of adipogenesis.

RNA Interference (RNAi)

Another embodiment of the invention comprises an isolated nucleotide sequence capable of inhibiting CCPG translation generally known as an antisense nucleotide, small interference RNA, or RNA interference (RNAi). RNA interference or "RNAi" is a term initially coined by Fire and co-workers to describe the observation that double-stranded RNA (dsRNA) can block gene expression when it is introduced into worms (Fire et al. (1998) Nature 391, 806 811, incorporated herein by reference). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The use of RNAi has been further described in Carthew et al. (2001) Current Opinions in Cell Biology 13, 244 248, and Elbashir et al. (2001) Nature 411, 494 498, both of which are incorporated herein by reference. Also, see, e.g., U.S. Pat. Nos. 7,022,828, 7,150,970, 7,101, 991, and 7,078,196, which are herein incorporate by reference. The RNAi molecules of the present invention are double-stranded or single-stranded RNA of from about 10 to about 100 nucleotides that inhibit RNA translation. That is, the isolated RNAi of the present invention mediate degradation of mRNA of the CCPG gene, thereby preventing its translation and reducing CCPG available for activation of PPARγ, and subsequently adipogenic gene transcription. By way of example but not of limitation, an RNAi containing the appropriate homology is set forth in sequences SEQ ID NO:11 and SEQ ID NO:12.

CCPG Vectors and Viral Delivery Systems

The nucleotide sequences may be used per se or further inserted into a suitable expression vector such as a plasmid or viral vector construct. Therefore, another embodiment is an expression vector capable of expressing a nucleotide sequence encoding the CCPG polypeptide such that when the CCPG polypeptide is expressed it may interact with nuclear receptors including PPARγ. Yet another embodiment is an expression vector encoding a RNAi capable of inhibiting CCPG expression. A verity of expression or transfection vectors are known in the art and are commercially available as are methods to insert these nucleotide sequences encoding polypeptides or RNAi of interest. Once the coding sequence of one or more CCPG polypeptides has been obtained, it may be operably linked to suitable control elements to provide an expressible nucleotide sequence using standard cloning or molecular biology techniques. See, e.g., Edge (1981) Nature 292:756; Nambair et al. (1984) Science 223:1299; and Jay et al. (1984) J. Biol. Chem. 259:6311. Expression vectors that may be effective for the expression of CCPG polypeptides that activate PPARγ include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSHIPERV (Stratagene, La Jolla Calif.), and PTET-OFF, PTET-ON, PTRE2, PTRE2-LUC, PTK-HYG (Clontech, Palo Alto Calif.). CCPG polypeptides may be expressed using (i) a constitutively active promoter, (e.g., from cytomegalovirus (CMV), Rous sarcoma virus (RSV), SV40 virus, thymidine kinase (TK), or P.beta.actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRXR and PIND; Invitrogen); the FK506/rapanmycin inducible promoter; or the RU486/mifepristone inducible promoter (Rossi, F. M. V. and Blau, H. M. supra)), or (iii) a tissue-specific promoter or the native promoter of the endogenous gene encoding leptin from a normal individual.

Once constructed, the nucleotide sequences including those that incorporate RNAi may be administered using standard gene delivery protocols. Methods for gene delivery are known in the art, including but not limited to methods based on naked nucleic acids, liposomes, cells, retrovirus including lentiviruses, adenovirus and parvoviruses including adeno-associated virus herpes simplex virus. See, e.g., U.S. Pat. Nos. 5,589,466, 6,936,272, 5,399,346, 6,818,209, 7,232,899, and 6,106,826 which are hereby incorporated by reference. Other gene delivery mechanisms include liposome-derived systems, artificial viral envelopes, and other systems known in the art (See, e.g., Rossi, J. J. (1995) Br. Med. Bull. 51(1): 217-225; Boado, R. J. et al. (1998) J. Pharm. Sci. 87(11): 1308-1315; and Morris, M. C. et al. (1997) Nucleic Acids Res. 25(14):2730-2736; El-Aneed, (2004) J Control Release 94, 1-14 all, herein incorporated by reference). Lentiviruses have been used for small interfering RNA and described (Li and Rossi (2005) Methods Enzymol 392, 226) and hereby incorporated by reference.

Administration of Nucleotides Encoding CCPG or RNAi

The various embodiment described herein are water-soluble and may be administered, by way of example, in a sterile aqueous solution, preferably a physiological solution. A pharmaceutically acceptable formulation of the present invention may be any injectable or topically applied physiological solution. A physiological solution may be comprised of isotonic balanced salts with a pH of about 7.0 to about 7.5. A preferred physiological solution may comprise isotonic saline and a pH of 7.5. For a topical administration or for certain targeted applications it may be desirable to increase the viscosity of the formulation. Various carries known to increase viscosity include but are not limited to such high molecular weight polymers such as, hyaluronic acid, hydroxypropyl methyl cellulose, as well as other carbohydrates or sugars. These are typical included in the formulation at 0.01 to 0.1 percent, 0.1 to 1.0 percent, 1 to 2 percent, 2 to 3 percent, 3 to 4 percent, 4 to 5 percent 5 to 10 percent, or 10 to 20 percent by weight. By way of example and not of limitation, recombinant viruses may be administered at a dose of $10^7$-$10^{12}$ pfu for a non-intravenous administration.

A wide variety of administration routes may be employed. The route, by which the nucleotide sequence or virus is administered, as well as the formulation, carrier, or vehicle, will depend on the target site as well as the desired effect. For example, if systemic administration is desired any intravenously or intravascularly injection may be employed. A single-time (bolus) injection is a possibility, as is continuous infusion. Alternatively, if a targeted administration is desired, a subcutaneous injection, or application to exposed tissues during course of surgery may also be employed. It may be desirable to administer CCPG encoding nucleotides as an adjunct to surgical procedure. By way of example, CCPG encoding nucleotides may be applied directly to tissue exposed during surgery. Promoting the genesis adipose tissue may be desirable for filling or augmenting soft tissue during cosmetic or reconstructive surgery. Various methods of administrating nucleotide sequence in vivo including vectors and delivery systems are further described by Mah et al., including organ targeted delivery, microencapsulation of recombinant cells, ex vivo transduction of stem cells, systemic delivery and vector targeting, (for review see Mah et al., (2002) Clin Pharmacokinet 41, 901-911 herein incorporated by reference). By way of example, for targeted soft tissue injections, recombinant viruses can be diluted in Dextrose-5 percent in a total volume that is 5-30 percent of the total estimated volume of a lesion to be injected. The recombinant virus can be administered by multiple injections at approximately 1 cm increments, three-dimensionally to cover the entire lesion. Virus may be administered multiple times depending on safety and efficacy.

The foregoing disclosure of methods for the administration of nucleotide sequences encoding CCPG polypeptides, applies equally to nucleotide sequence encoding RNAi for regulation of adipogenesis.

Applications

The CCPG nucleic acids and proteins of the invention are useful in potential diagnostic and therapeutic applications and as research tools. These include serving as a specific or selective nucleic acid or protein diagnostic and/or prognostic marker, wherein the presence or amount of the nucleic acid or the protein are to be assessed. These also include potential therapeutic applications such as the following: (i) a protein therapeutic; (ii) a small molecule drug target; (iii) an antibody target (therapeutic, diagnostic, drug targeting/cytotoxic antibody); (iv) as described above, a nucleic acid useful in gene therapy (gene delivery/gene ablation); and (v) and an agent promoting tissue regeneration in vitro and in vivo.

There is a multitude of conditions in which it may be desirable to modulate the generation of adipose tissue. Conditions in which it would be desirable to promote generation of adipose tissue include but are not limited to, subjects suffering from wasting diseases, subjects chronically underweight, livestock underweight, subjects undergoing cosmetic or reconstructive surgery, or, treatment in place of cosmetic or reconstructive surgery. Conditions in which it would be desirable to inhibit the generation of adipose tissue include but are not limited to, subject chronically overweight, subjects suffering from obesity, subjects undergoing cosmetic or reconstructive surgery or, treatment in place of cosmetic or reconstructive surgery. Also included are in vitro applications. Any application where cell differentiation is critical to success in the development of therapeutic strategies. By way of example stem cells, mesenchyme cells, and preadipose cells, which may be used in transplantation, ex vivo tissue reconstruction or tissue engineering (see Patrick et al., (2001) The Anatomical Record, 263:361-366). It may be desirable to prevent, enhance, or inhibit adipogenesis in these cells. By way of example, it may be desirable to repress adipogenetic gene expression in cells used for reconstruction of bone or cartilage tissue. Alternatively, it may be desirable to induce adipogenic tissue for cosmetic or reconstitute surgery by way of example for filling a soft tissue defect.

DEFINITIONS

The term "CCPG" or "PGCC" refers to a Constitutive Coactivator of PPARgamma of the instance invention, a polypeptide with properties that include that of a coactivator or the regulation or modulation of nuclear transcription factor PPARγ.

The term "CCPG polypeptide" refers to a CCPG from any source or a fragment of a CCPG from any source with PPARγ transcriptional regulating or modulating activity.

The term "adipogenesis modulating factor" means any agent that enhances or inhibits the interactions of transcriptional factors capable or promoting adipogenesis.

The term "adipogenesis" and "influencing adipogenesis," regulating adipogenesis, or modulating adipogenesis as used herein refers to any increase or decrease of adipogenic gene expression or expression of adipocyte-specific markers, including but not limited to the expression of adiponectin and perilipin polypeptides or their related nucleotide sequences. Also included is any increase in the accumulation of fats or oils within cell compartments or the differentiation of a cell to an adipocyte by any detectable means including morphological.

The term "coactivator" or "coactivating" as used herein refers to any composition including a protein, polypeptide, amino acid sequence, nucleotide sequence, or fragment thereof or small molecule mimic thereof which activates PPARγ and enhances or increases PPAR transcription promoting activity.

The term "corepresor" or "corepressing" as used herein refers to any composition including a protein, polypeptide, amino acid sequence, nucleotide sequence, or fragment thereof or small molecule mimic thereof which represses PPARγ activation and inhibits or decreases PPAR transcription activity.

The acronym "CREB" as used herein refers to cAMP-response element-binding protein.

The term "reporter" as used herein refers to chemical or enzymatic markers that may be attached to a nucleotide or amino acid sequence, allowing the identification and/or localization of theses molecules. By way of example, fluorescent reporters such as fluorescence or rhodamine, enzyme reporters such as horseradish peroxidase, alkaline phosphatase, or radioactive isotopes, may be attached to a nucleotide or amino acid sequence.

The term "PPARγ reporter" as used herein refers to a nucleotide sequence operably linked to a reporter such that initiation of transcription of the nucleotide sequence by PPAR γ results in expression or activation of the reporter including but not limited to the PPARγ-responsive luciferase reporter construct PPRE-TK-LUC.

The acronym "NR" as used herein refers to Nuclear receptor.

The acronym "PGC-1" as used herein refers to PPARγ coactivator-1.

The acronym "CCPG" as used herein refers to PPAR gamma constitutive coactivator-1.

The acronym "PPAR" as used herein refers to peroxisome proliferators activated receptor.

The acronym "PPRE" as used herein refers to peroxisome proliferator response elements.

The acronym "RXR" as used herein refers to retinoid X receptor.

The acronym "SRC" as used herein refers to steroid receptor coactivator.

The acronym "TFIIH" as used herein refers to transcription initiation factor IIH.

The acronym "TRAP" as used herein refers to thyroid hormone receptor-associated protein The acronym "Tro" as used herein refers to troglitazone.

The acronym "XPG-like" as used herein refers to xeroderma pigmentosum group G-like.

The term "vector" or "expression vector" as used herein refers to a polynucleotide that enables the expression of a constituent polynucleotide in a cell, wherein expression means the transcription of DNA into RNA. Vectors include any and all plasmids of viral vectors including retroviral vectors, such as pLin for the expression of antisense polynucleotides, and vectors that enable the continuous or stable expression of siRNAs, such as pSUPER.

The term "transfection" refers to the introduction of a vector in to a cell whereby the vector is expressed. By way of example these methods include naked nucleotides per se, viral deliver systems, liposomes, use of $Ca^{2+}$ in culture media, cell fusion. Transfection may take place in vivo including introducing the vector to an human or animal, or ma take place in vitro, including cell culture conditions.

The term "cell" as used herein refers to a eukaryotic cell, preferable a mammilla cell. Cells may exist in vitro including in an animal, or in vivo including in cell culture.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent Identity" or of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g. XBLAST and NBLAST) are used.

Table 1 shows the calculations of identity for comparisons of CCPG polypeptides from various mammalian species relative to mouse CCPG.

TABLE 1

Percent Identity of CCPG Amino Acid Sequences

| Species (Nucleotide Accession Number) | Amino Acid Accession Number | Percent Identity |
|---|---|---|
| Mouse (DQ873694) | ABH09085 | 100 |
| Human (DQ873695) | ABH09086 | 67 |
| Rat (XM_218006) | XP_218006 | 92 |
| Canine (XM_855466) | XP_855466 | 79 |
| Bovine (XM_602628) | XP_602628 | 67 |

TABLE 2

| Species (Amino Acid Residues) | Amino Acid Accession Number | Percent Identity |
|---|---|---|
| Mouse (1-320) | ABH09085 | 100 |
| Human (1-320) | ABH09086 | 87 |
| Mouse (420-786) | ABH09085 | 100 |
| Human (420-786) | ABH09086 | 80 |

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with other embodiments possible within the scope and spirit of this disclosure.

EXAMPLES

As illustrated in the examples below, the inventor has identified and characterized a novel PPARγ coactivator CCPG, and explored its role in promoting PPARγ-directed adipogenesis. The ability of CCPG in PPARγ transactivation is similar to PGC-1α. However, it was determined that interactions between CCPG and PPARγ were independent of PPARγ ligand binding. CCPG may enhance PPARγ function by synergizing ligand-stimulated PPARγ transactivation, even though the CCPG-PPARγ interaction is not influenced by ligand or by recruiting other transcription related proteins that promote PPARγ activity.

It was determined that CCPG has multiple sites in contact with PPARγ. Mutation of all 4 LXXLL motifs of CCPG did not compromise its interaction with PPARγ, implying novel structural characteristics present in CCPG. Though CCPG is ubiquitously expressed and interacts with PPARγD hinge region, and PGC-1α interacts with part of PPARγ DNA binding and D hinge region (36), a direct interaction between CCPG and PGC-1α by Co-IP was not observed (data not show). Nonetheless, a synergistic effect was seen in the in vitro PPRE luciferase reporter assay when CCPG and PGC-1α were co-expressed. This effect can be reconciled since both CCPG and PGC-1α are coactivators for PPARγ. The sequential assembling of transcription machinery is a complex process involving participation of many transcription factors, coactivators, and corepressors which play different roles. The different expression profiles of CCPG and PGC-1α also reflect their distinct roles in adipogenesis. The inventor further found that CCPG interacts with RXRα and ERα, but not with TRβ, suggesting CCPG may act as a selective coactivator for certain NRs.

A structure prediction reveals a Xeroderma pigmentosum G-like (XPG like) domain containing a helix-hairpin-helix (HhH)2 motif located in CCPG N-terminus. This characteristic domain is observed in DNA repair enzymes and in DNA polymerases (Sancar et al. (2004) Annual Review of Biochemistry 73, 39-85). The HhH2 motif is capable of binding to single-stranded DNA (Tsodikov et al. (2005) Proceedings of the National Academy of Sciences 102, 11236-11241) and plays a role in segregating achiasmate chromosomes during meiosis (Cui and Hawley (2005) Genetics 171, 1823-1835), probably facilitating to form an opening transcriptional complex in the promoter region. The highest expression levels of CCPG in testis may be related to this process. The inventor speculated that upon unwinding double stranded DNA in the promoter region, CCPG may bind to single-stranded DNA with its HhH2 motif and interacts with the hinge region of PPARγ to accelerate transcription. However, more detailed studies are warranted to answer whether CCPG bears nuclease activity and plays a role in DNA repair and replication.

CCPG truncation studies have shown that the N-terminus of CCPG (1-561) possesses an activating function for PPARγ, and its C-terminus acts as an inhibitor of PPARγ activation. These opposing functions may work to precisely regulate PPARγ activate. The modulation of CCPG on PPARγ transactivation and adipogenesis was explored in cell culture. It was demonstrated that CCPG promotes adipogenesis of OP9 preadipocytes when CCPG was introduced in to cells. Furthermore it was determined that when interfering RNA was used to disrupt translation of CCPG, adipogenesis was inhibited.

The following examples support that CCPG may enhance PPARγ function by synergizing ligand-stimulated PPARγ transactivation even though the CCPG-PPARγ interaction is not influenced by ligand binding or by recruiting other transcription related proteins that promote PPARγ activity.

In summary, the inventor discloses that CCPG, which not only interacts with PPARγ but also with RXRα and ERα, is a bona fide coactivator for PPARγ that promotes adipogenesis. CCPG may be manipulated to regulate PPARγ transactivation and adipogenesis as demonstrated by transfection of a preadipocyte nucleotide encoding a CCPG or an RNAi targeting CCPG translation. Moreover, CCPG promoted adipogenesis may have certain roles in obesity and disruption of CCPG-PPARγ interaction may provide a new method for the prevention and therapy of obesity and related disorders.

Materials and Methods

Elements of the inventor's methodology not described herein are generally well known and detailed in numerous laboratory protocols, including Molecular Cloning 2nd edition, (1989) Sambrook, J., Fritsch, E. F., and Maniatis, J., Cold Spring Harbor., and Current Protocols in Molecular Biology, volumes 1-3, John Wiley and Sons, Inc. herein incorporated by reference.

Cells, Plasmid, Antibodies, and Animals. HCT-116, COS7, and NIH3T3 cells were cultured in medium recommended by American Type Culture Collection (ATCC, Manassas, Va.). On the day of transfection, the medium was switched to medium containing 10 percent charcoal/dextran-treated FBS (Hyclone, Logan, Utah). PPAR reporter plasmid PPRE-TK-LUC, RXRα and PPARγ expression constructs were described previously (Zhu et al. (1996) Gene Expr 6, 185-195; Zhu et al. (1997) J Biol Chem 272, 25500-25506) and were used as PCR templates. PGC-1α expression plasmid was from Addgene (Cambridge, Mass.) (Puigserver et al.

(1998) Cell 92, 829-839). The CCPG mutant (LXXLL to LXXAA) expression constructs were generated using GeneTailor site-directed mutagenesis kit (Invitrogen). All other expression constructs were generated by PCR cloning and validated by DNA sequencing. A rabbit anti-CCPG antibody was generated using synthesized peptide GILGEDTDYLIY-DTC (SEQ ID NO:13) as antigen (Lampire Biological Laboratories, PA). Adiponectin and perilipin antibodies were from Sigma (St. Louis, Mo.). All other antibodies were purchased from Santa Cruz Biotechnology (Santa Cruz, Calif.). All protocols and procedures were approved by the Animal Care and Use Committee of Saint Louis University and followed the NIH Guide for the Care and Use of Laboratory Animals. Mouse tissues were removed and collected from male (8 weeks old) or female pregnant C57BL/6 mice (Jackson Laboratories) at the specified time points after halothane overdose inhalation.

Northern and Western Blot Analyses. Total RNA (25 µg) isolated from mouse tissues or embryos were separated on 1 percent formaldehyde agarose gels and transferred to nitrocellulose membranes. The 1.5 kb DIG-labeled CCPG cDNA probe was hybridized with the membranes overnight. The membrane was visualized using an HRP-conjugated anti-DIG antibody (Roche, Indianapolis, Ind.). Western blots were performed according to the methods reported previously (Tong et al. (2006) Am. J. Respir. Cell Mol. Biol. 34, 28-38).

Transient Transfection and Reporter Assay. HCT-116 cells were co-transfected with plasmids as indicated. After 5 hour incubation, cells were treated with appropriate medium supplemented with 10 percent charcoal/dextran-treated FBS (Hyclone) and 1.0 µM Tro or 0.1 percent vehicle (DMSO). The luciferase activity was measured 16-20 h after transfection and the transfection efficiency was normalized by dividing the firefly luciferase activity by the *Renilla* luciferase activity according to the Dual-Luciferase Reporter Assay kit manual (Promega, Madison, Wis.).

Real-time RT-PCR. Total RNAs were isolated using Trizol reagent (Invitrogen) and reverse-transcribed into First-Stranded cDNAs (Roche). Real-time RT-PCR of CCPG expression was performed using the SYBR Green PCR Master Mix and ABI Prism 7700 Sequence Detector (Applied Biosystems) with forward primer 5'-GAA GCA CTC ATG TGT ACA CAC CCTG-3' (SEQ ID NO:14) and reverse primer 5'-CCA CTC CTT GAC CAC TGG GCC AG-3'. (SEQ ID NO:15) The value of each sample was normalized to that of GAPDH.

Adenovirus Preparation. cDNA encoding GFP or GFP-CCPG was inserted into the pAd/CMV-V5-DEST Gateway adenoviral vector and the adenoviruses of Ad-GFP and Ad-CCPG were prepared and titrated in 293A cells according to the manufacturer's instructions (Invitrogen, Grand Island, N.Y.). The adenovirus-delivered small hairpin RNA interference (shRNAi) was used to knockdown target gene expression. Briefly, oligonucleotides representing CCPG or LacZ used as negative control (provided by Invirogen) were annealed, cloned into pENTR/H1/TO vector (Invitrogen), then subcloned into adenoviral vector pAd/BLOCK-iT-DEST (Invitrogen) according to the manufacturer's instructions. The sense strands of the CCPG RNAi and its mutant sequence were as follows (including linkers): CCPG RNAi1 5'-CAC CGC AAA TGG TGA GTT TAA ATC CCG AAG GAT TTA AAC TCA CCA TTT GC-3, (SEQ ID NO:11) and CCPG RNAi2 5'-CAC CGC CCA CAC ATA TGT ACC ATA GCG AAC TAT GGT ACA TAT GTG TGG GC-3' (SEQ ID NO:12). For the CCPG RNAi control, the mutated sequence from CCPG RNAi2 was 5'-CAC CGC TTA GAG ATA ACA ACC ATA GCG AAC TAT GGT TGT TAT CTC TAA GC-3' (SEQ ID NO:16), which has been shown no significant similarity found in BLAST search.

Example 1

Cloning, Expression, and Subcellular Localization of CCPG

CCPG was identified, cloned, characterized, and localized at the subcellular level as follows. The inventor performed a cDNA microarray (Incyte Genomics, 9400 gene elements) on hypoxia-treated mouse lungs (10 percent $O^2$ for 4 days) and found that Expressed Sequence Tag (EST) W62706 was increased 2.7-fold among 270 unregulated genes (data not shown) (Teng et al. (2003) Circ Res 92, 1065-1067). The nucleotide sequence of EST W62706 was used to search the GenBank database and was found to be homologous to the transcript (accession number: NM_024203) encoding an uncharacterized KIAA1838-like protein. Based on the sequence information, the inventor then cloned the full-length cDNA sequence using Rapid Amplification of cDNA Ends (RACE) (GenBank accession number: DQ873694). For 5'-RACE, first-strand cDNA was synthesized by using CCPG gene-specific primer 5'-GAG ACA GCA CAT GGC GTC CAC CAC G-3' (SEQ ID NO:17) and adult mouse lung total RNA as template. An oligo-dT anchor primer 5'-GAC CAC GCG TAT CGA TGT CGA CTT TTT TTT TTT TTT TT(A/C/G)-3' (SEQ ID NO:18), and a nested CCPG gene specific primer 5'-GGT GAC GCT CTG CCA GCT CGT GG-3' (SEQ ID NO:19), were used to amplify the 5'-end of CCPG cDNA. For 3'-RACE, first-strand cDNA was synthesized by using above oligo-dT anchor primer. The 3'-end of CCPG cDNA was amplified by using the primer 5'-GAC CAC GCG TAT CGA TGT C-3' (SEQ ID NO:20), and the CCPG specific primer 5'-CGT AGG CAG AAC GCA TTG GGA CTC-3'. (SEQ ID NO:21), To investigate the function of the protein encoded by this novel cDNA, the inventor performed yeast 2-hybrid screening for its potential interaction partner(s). The yeast two-hybrid screen was performed following the Matchmaker GAL4 Two-Hybrid System 3 kit (Clontech) protocol. The CCPG cDNA was inserted into the GAL4 DNA-binding domain of pGBKT7 bait plasmid (pGBKT7-CCPG) and used to screen a mouse 17-day embryo cDNA library constructed in the pACT2 plasmid expressing the GAL4 activation domain. pGBKT7-CCPG was transformed into yeast AH109 and maintained in tryptophan-Dropout medium (AH109-CCPG). The mouse 17-day embryo cDNA library was transformed into yeast AH109-CCPG, and positive colonies appeared in blue on X-α-Gal containing medium due to secretion of α-galactosidase.

Using this cDNA as bait, the 17-day mouse embryo cDNA ($1.4 \times 10^6$ clones) library was screened and yielded 13 strong positive colonies under high stringency selection strategy. One of the positive clones encoded the nuclear receptor PPARγ. Further study demonstrated that this protein is constitutively expressed in multiple adult mouse tissues and throughout embryonic development. It enhanced PPARγ activity and was thereafter designated Constitutive Coactivator of PPAR gamma, or CCPG. Efforts have focused on the investigation of the roles that CCPG plays in the interaction, regulation of PPARγ transactivation, and adipogenesis. Northern blots showed that the transcript of mouse CCPG was ~3.0 kb long encoding a protein of 786 amino acid residues with 4 characteristic LXXLL (L for Leucine and X for any amino acid) motifs.

Figure 3:
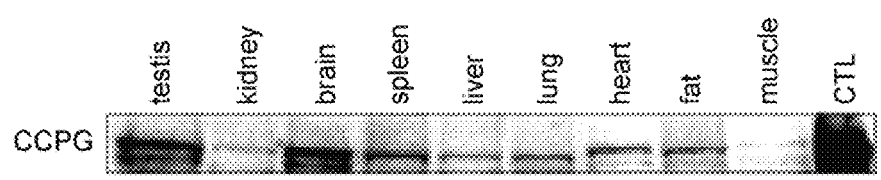
FIG. 3 illustrates the expression profile and subcellular localization of CCPG. CCPG protein (A and C) and mRNA (B and D) expression in adult mouse tissues and embryos from embryonic day (E) 5 through E19 and pregnant mouse placenta and uterus (E13). CTL represents 293 cell lysate expressing the recombinant mouse CCPG. Protein (100 μg) or 25 μg total RNA isolated from various mouse tissues, embryos (E5 through E19), placenta and pregnant mouse uterus (E13) were used. Ethidium bromide (EtBr) staining of 18S/28S RNA was used as loading control. (E) CCPG is localized in the nucleus. 3T3 cells were transfected with GFP-fused full-length CCPG. Cells were examined and photographed under a fluorescence microscopy (400×) 24 hr after transfection. Scale bar equals 10 μm.
Figure 3:
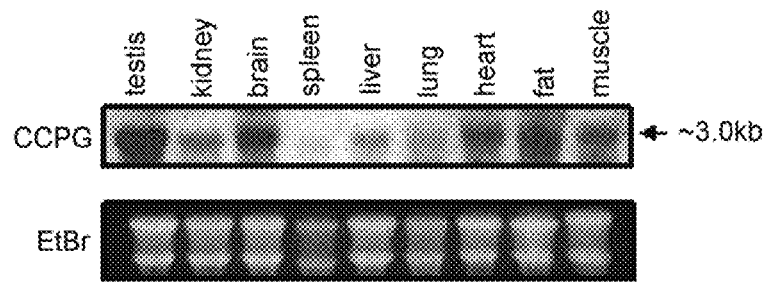
Figure 3:
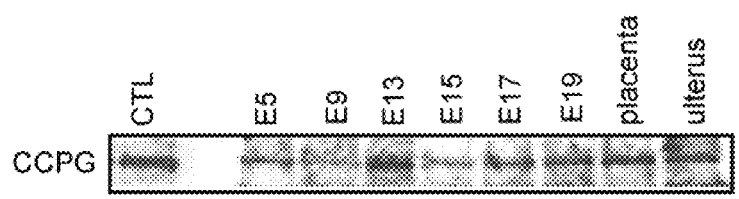
Figure 3:
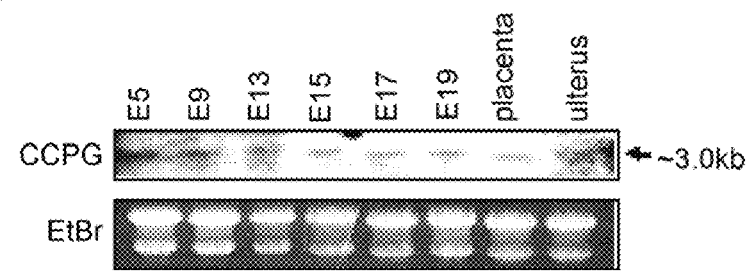
Figure 3:
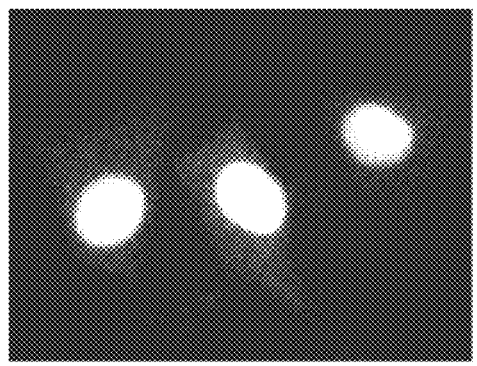

The inventor has identified its human (GenBank accession number: DQ873695), mouse (DQ873694), rat (XM_218006), dog (XP_855466), and cattle (XP_602628) homolog either with cDNA cloning (for mouse and human) or by searching current available databases, and found they were highly conserved (FIG. 2A). A search for the human homolog revealed a human nucleotide sequence NW_923184 associated with chromosome 6, for which no polypeptide was known. Using methodology described above for mouse, the inventor cloned a novel human nucleotide sequence (SEQ ID NO:7) which expresses a novel human CCPG polypeptide (SEQ ID NO:2). An analysis of protein sequence alignment indicates that CCPG is composed of an N-terminal conserved XPG-like (xeroderma pigmentosum group G-like) domain (XLD) containing one LXXLL motif, a central variable hinge region (CVR), and a C-terminal conserved domain (CCD) containing 3 LXXLL motifs (FIG. 2B). A rabbit polyclonal antibody against mouse CCPG was raised using a synthetic peptide (GILGEDTDYLIYDTC) as antigen and mouse CCPG was found to be expressed as a ~95 KD molecular weight protein in HEK 293 cells (FIG. 2C). Gene structure analysis indicates that CCPG from mouse and human consists of 11 exons and 10 introns, and is localized at chromosome 17(A1) in mice and 6q26-27 in humans. Northern and western blots showed that CCPG was expressed in all adult mouse tissues examined with the higher expression in testis, brain, spleen, heart, and fat tissues (FIGS. 3A and 3B). A time-course examination also showed that CCPG was expressed throughout the embryonic developmental stages from embryonic day 5 (E5) through E19, as well as in placenta and uterus of pregnant mouse (E13) (FIGS. 3C and 3D). To determine its subcellular localization, CCPG was fused in-frame with GFP (GFP-CCPG), and when expressed in NIH3T3 cells, it localized entirely to the nucleus of the cells (FIG. 3E).

Example 2

Characterization of CCPG-PPARγ and Other NR Interactions

GST pull-down assays were performed to investigate CCPG interactions, and showed that CCPG interacts with PPARγ, RXRα, and ERα but not TRβ. GST or GST-CCPG fusion protein (subcloned into the pGEX-4T-2 vector) was expressed in *E. coli*. BL21 and purified by glutathione Sepharose 4B affinity chromatography (Amersham, Piscataway, N.J.). COS7 cells were transfected with appropriately tagged expression constructs or control plasmid DNA. Cell lysates were incubated in binding buffer (50 mM HEPES pH 7.5, 120 mM NaCl, 1 mM EDTA, 1 mM DTT, 0.5 percent NP-40, 10 percent glycerol) plus a protein inhibitor cocktail (Roche) with ~20 μg of purified GST or GST-CCPG fusion protein immobilized on glutathione-conjugated Sepharose 4B beads in the presence of ligand or vehicle (10 μM Tro and 10 μM 9-cis retinoid acid) for at least 3 hr, and washed with binding buffer 4 times. Beads were boiled in protein 1×SDS-PAGE loading buffer and the supernatants were analyzed by western blot.

Figure 4A:
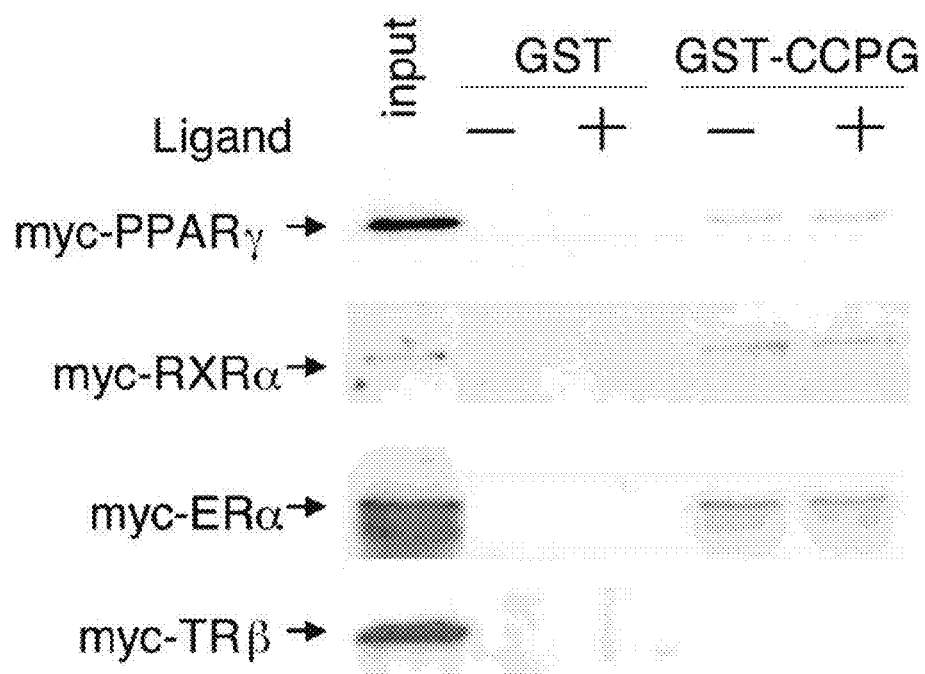
FIG. 4 illustrates CCPG interaction with PPARγ and other nuclear receptors in a ligand-independent manner. (A) For GST pull-down assays, COS7 cells were transfected with myc-tagged PPARγ, RXRα, ERα, or TRβ. The cell lysates were incubated with 20 μg of purified GST or GST-CCPG protein immobilized on glutathione Sepharose beads in the presence (+) or absence (−) of ligand. For PPARγ. Tro was used at 10 μM; for RXRα, 9-cis RA was used at 10 μM; for ERα, 17β-estrodiol was used at 1 μM; and for TRβ, T3 was used at 1 μM; 10 percent of protein was used as input loading for each pull-down, except that 5 percent was used for RXRα. HRP-conjugated anti-myc antibodies were used to detect the interactions. Please note that the input proteins are 1/10 for PPARγ, ERα and TRβ and 1/15 for RXRα of the pulldown reactions. (B) For co-IP, HCT-116 cells were co-transfected with Flag-tagged PPARγ plus GFP or GFP-CCPG and treated with 1.0 μM Tro or 0.1 percent vehicle (DMSO). Cell lysates were incubated with anti-GFP antibody, and PPARγ was detected by western blotting with HRP-conjugated anti-Flag antibody. After stripping, the membrane was reprobed with anti-GFP or anti-GAPDH antibody, respectively.

To determine whether CCPG interacts with NRs, Myc-tagged PPARγ, RXRα, ERα, and TRβ were expressed in COS7 cells and the resulting cell lysates were incubated with purified GST or CCPG-GST fusion protein immobilized on glutathione Sepharose 4B beads in the presence of ligand or vehicle as stated in figure legend. As shown in FIG. 4A, CCPG bound to PPARγ.RXRα and ERα, but not TRβ in a ligand-independent manner.

Example 3

CCPG Binds to PPARγ in a Ligand-Independent Manner

Figure 4B:
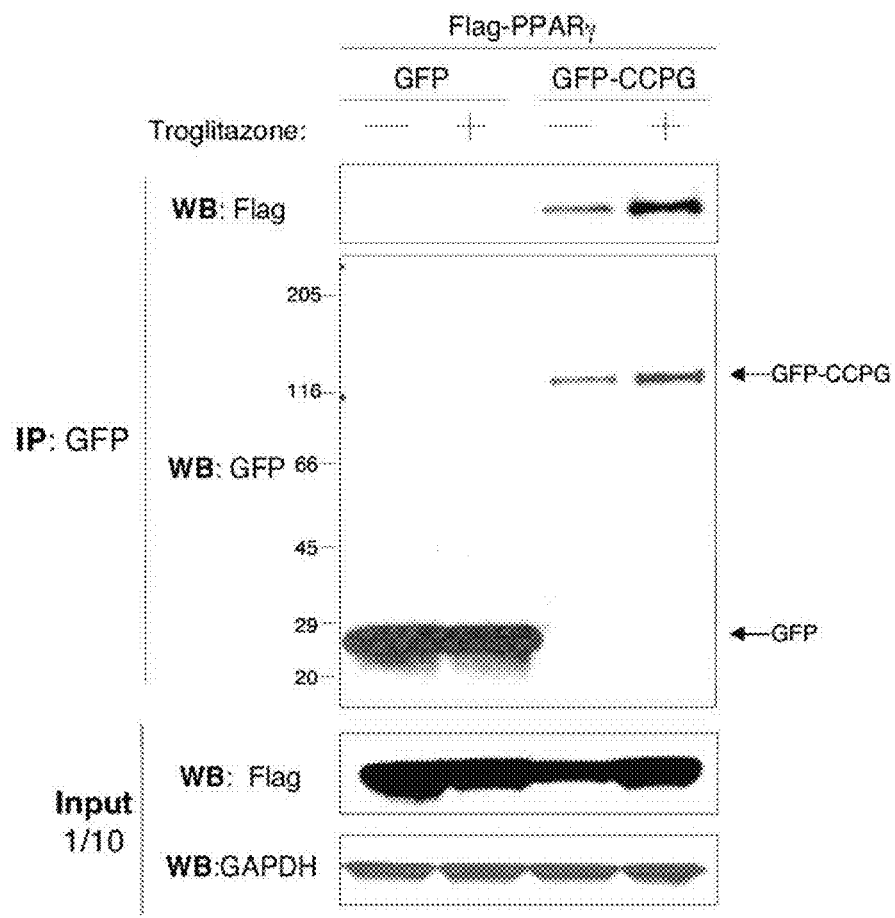

To further determine whether CCPG interacts with PPARγ in vivo, COS7 cells were co-transfected with Flag-tagged PPARγ with either GFP or GFP-tagged CCPG expression vector, and then co-immunoprecipitated (Co-IP) with anti-GFP antibody. COS7 cells were cotransfected with plasmid vectors expressing Flag-tagged PPARγ plus plasmid vector expressing GFP or various GFP-tagged proteins. For those ligand treatment assays, 16 hr after transfection, cells were treated with 1.0 μM Tro or vehicle (0.1 percent DMSO) for additional 2 hr before harvesting. Cells were then washed with phosphate-buffered saline twice and suspended in ice-cold IP binding buffer. For each IP assay, anti-GFP antibody was used to co-IP GFP or GFP fusion proteins in the presence or absence of NR ligands (10 μM Tro for PPARγ or 10 μM 9-cis retinoid acid for RXR) for 1 hr and then incubated with 50 μl of Protein A/G Plus agarose beads (Santa Cruz) for 3 hr at 4° C. Beads were washed with washing buffer 4 times at 4° C. Co-precipitated proteins were released by boiling the beads in 1×SDS-PAGE loading buffer and analyzed by western blot. Western blots showed that CCPG interacted with PPARγ in a ligand-independent manner (FIG. 4B). It was determined that CCPG interacts with PPARγ in vivo in a ligand-independent manner.

Example 4

CCPG Binds to the D Hinge Region of PPARγ

Figure 5:
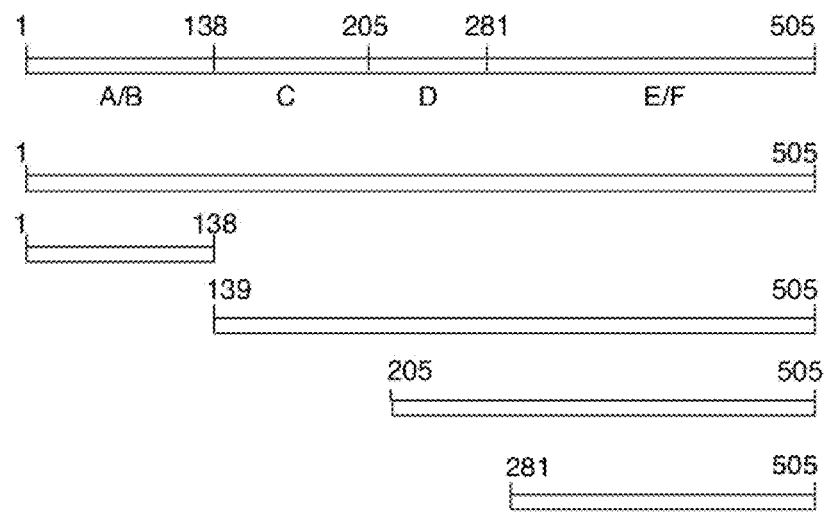
FIG. 5 illustrates the Characterization of PPARγ-CCPG interaction. (A) Diagram of different PPARγ deletions according to a PPARγ structure module. (B) GST pull-down assays were performed using COS7-expressed, myc-tagged, different PPARγ deletions and purified GST or GST-CCPG immobilized on glutathione Sepharose beads. The input lanes represent 10 percent of the total volume of the lysate used for the pull-downs for each sample. Interactions were detected by western blot with an anti-myc antibody. (C) Diagram of truncated N-terminal 1-561 and C-terminal 562-786 CCPG tagged with GFP. (D). Co-IPs were performed exactly as in FIG. 4B. (E) Diagram of GFP-tagged CCPG mutants with a series of mutated LXXLL motifs (LXXLL to LXXAA). (F) Co-IPs were performed exactly as in FIG. 4B.
Figure 5:
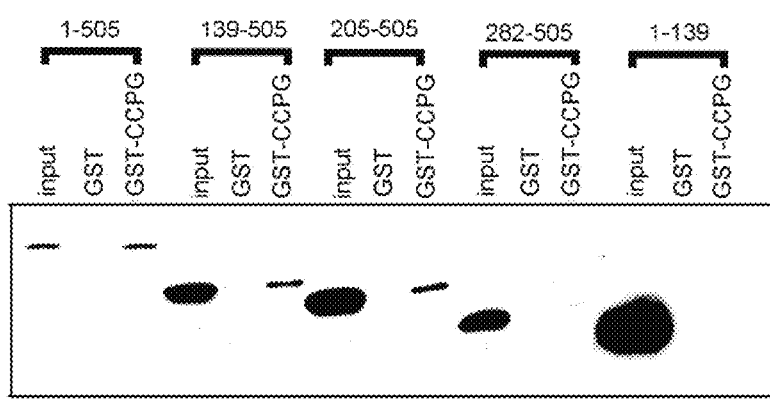
Figure 5:
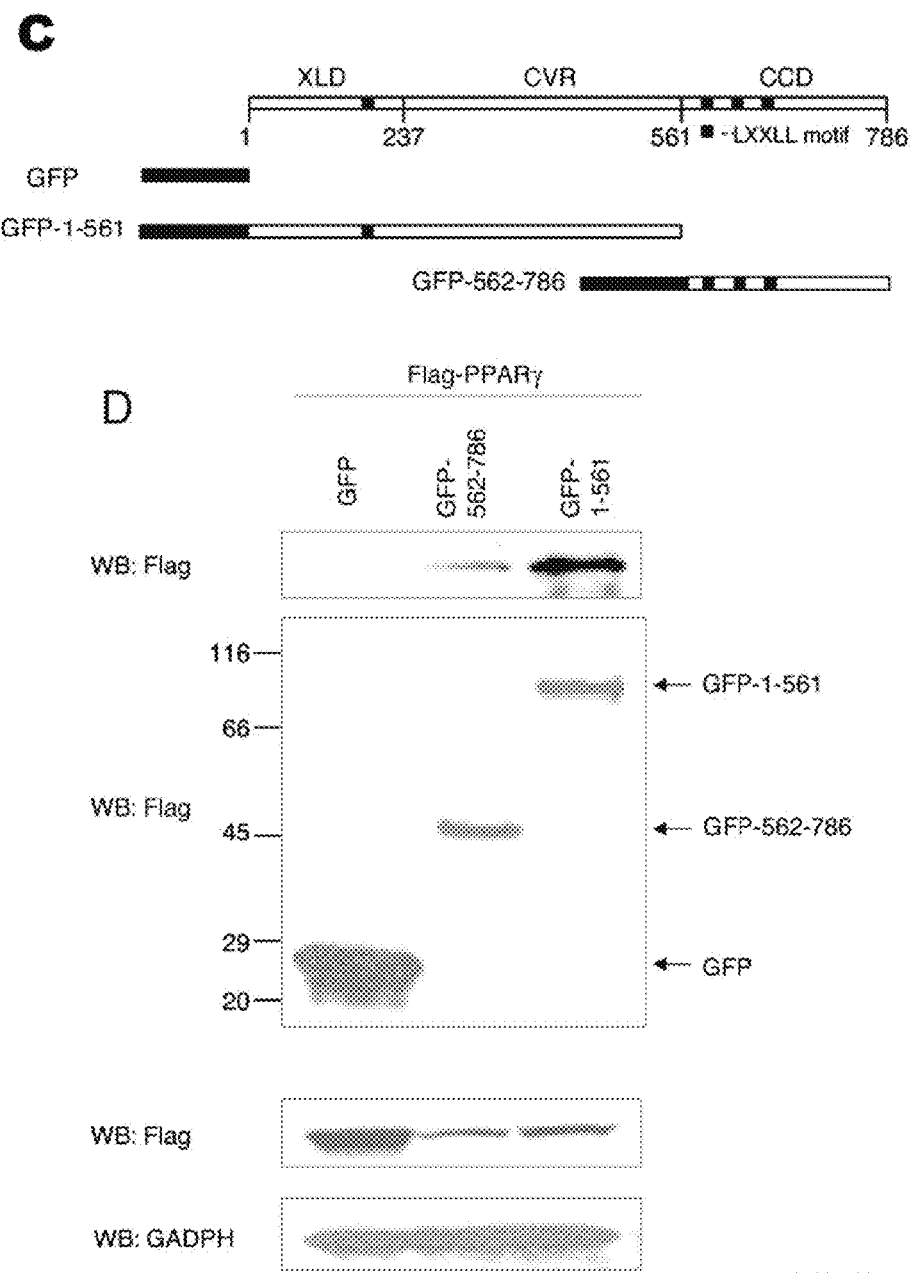

To map the domain in PPARγ that mediates CCPG-PPARγ interaction, the inventor generated C-terminal myc-tagged PPARγ truncated expression constructs with corresponding domain deletions based on a PPARγ structure module (FIG. 5A) (Rosen and Spiegelman (2001) J. Biol. Chem. 276, 37731-37734). Purified GST or GST-CCPG were incubated with COS7-expressed, myc-tagged PPARγ truncated protein. Co-IP with an anti-myc antibody was used to detect the interactions between CCPG and PPARγ truncates. As shown in FIG. 5B, full-length PPARγ and PPARγ with deletions of amino acids 1-205 still retained the binding ability to CCPG, but the more proximal PPARγAF1 domain (amino acids 1-138) or PPARγ with deletion of amino acids 1-281 had shown no ability to bind CCPG, indicating that the D hinge region of PPARγ spanning amino acid 205 to 280 is responsible for its interaction with CCPG.

Example 5

CCPG Utilizes its Multiple Sites to Interact with PPARγ

To determine the regions in CCPG that mediate its interaction with PPARγ, the inventor truncated CCPG in two large fragments: GFP-tagged CCPG N-terminus (1-561) and GFP-tagged C-terminus (562-786), respectively (FIG. 5C). Flag-tagged PPARγ was co-expressed either with GFP, or GFP-tagged CCPG fragments in COS7 cells. FIG. 5D showed that addition of GFP antibody resulted in Co-IP of Flag-PPARγ with both GFP-1-561 and GFP-562-786 of CCPG, but not with GFP alone, indicating that there are at least two regions in CCPG located in N-terminus and C-terminus interacting with PPARγ.

Example 6

The LXXLL Motifs in CCPG are not Required for its Interaction with PPARγ

Figure 5E:
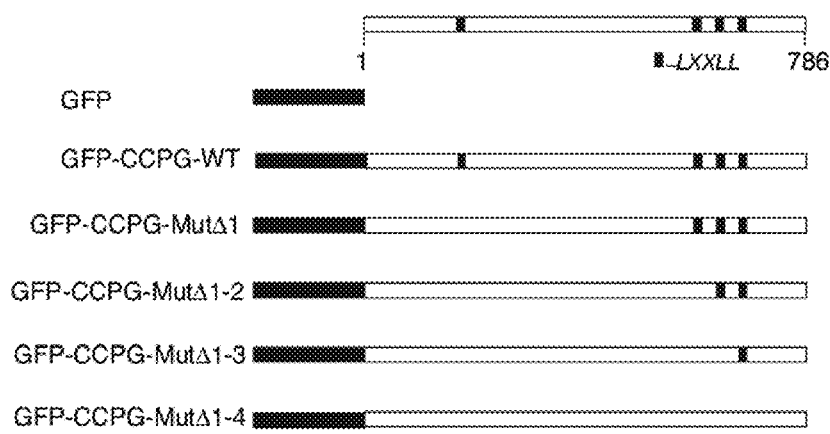
Figure 5F:
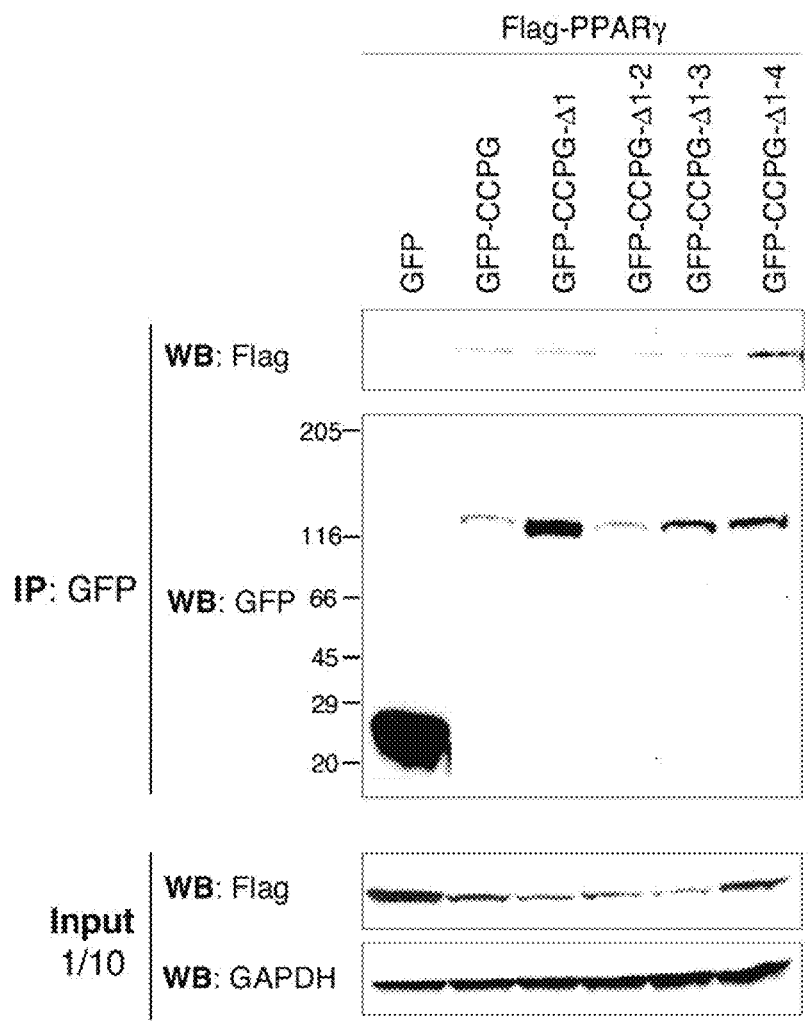

LXXLL motif has been thought to mediate ligand-dependent recruitment of p160-type of coactivator to nuclear receptor (Heery et al. (1997) Nature 387, 733-736; McInerney et al. (1998) Genes Dev. 12, 3357-3368). Notably, CCPG has four characteristic LXXLL motifs: one in the N-terminus and three in the C-terminus. The inventor subsequently examined whether the presence of LXXLL motifs in CCPG contributes to CCPG-PPARγ interaction. The inventor generated GFP-tagged CCPG mutants with a series of mutated LXXLL motifs (LXXLL to LXXAA) (FIG. 5E) and utilized co-IP assay to analyses their interactions with PPARγ. As shown in FIG. 5F, even CCPG mutated with all four LXXLL motifs did not compromise its binding to PPARγ. Thus, LXXLL motifs of CCPG were not required for its interaction with PPARγ, indicating the presence of novel structural motif(s) in CCPG responsible for its interaction with PPARγ.

Example 7

N-terminus of CCPG Enhances Transactivation of PPARγ

Figure 6:
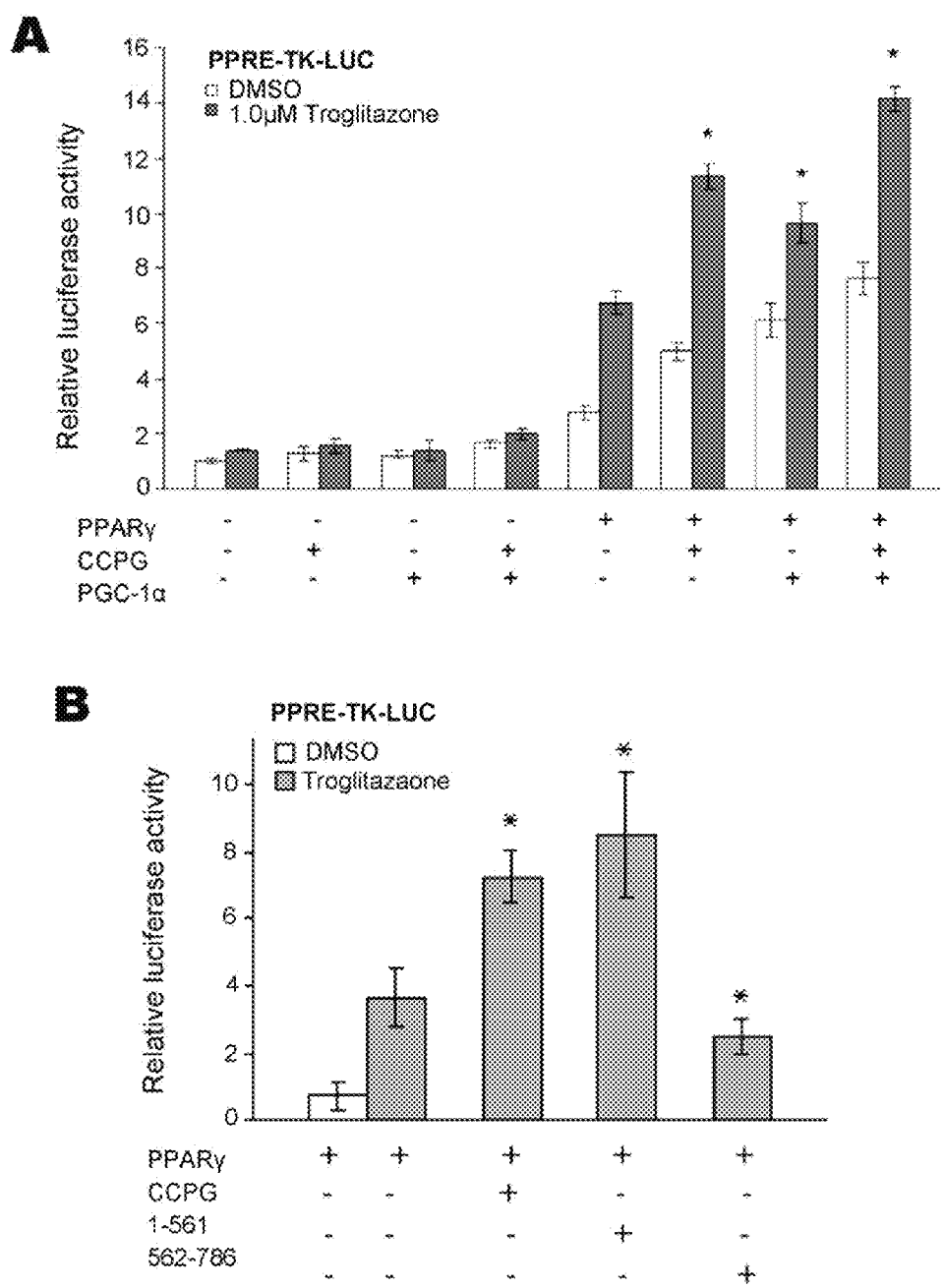
FIG. 6 illustrates CCPG coactivativation of PPARγ and ERα, and N-terminus of CCPG possesses an activation domain. (A) HCT-116 cells were cotransfected with 300 ng of PPRE-TK-LUC, 50 ng of PPARγ, 50 ng of CCPG and 25 ng of a previously identified PPAR coactivator PGC-1α expression plasmids with Tro (1.0 μM) or 0.1 percent vehicle (DMSO). (B) HCT-116 cells were cotransfected with 300 ng of PPRE-TK-LUC, 50 ng of PPARγ, either 50 ng of CCPG, CCPG 1-561 or CCPG 562-786 expression plasmids with Tro (1.0 μM) or 0.1 percent vehicle (DMSO). (C) HCT-116 cells were cotransfected with 150 ng of PPRE-TK-LUC, 50 ng of PPARγ, 50 ng of CCPG expression plasmids with increasing amount (5, 25, 100 ng) of CCPG 1-561 or CCPG 562-786 expression plasmid plus Tro (1.0 μM) or 0.1 percent vehicle (DMSO). Empty pcDNA3.1 plasmid was added to ensure equal DNA amount used in each transfection. (D) COS7 cells were cotransfected with the reporter plasmid pG5luc (Promega) containing five copies of the UAS linked to luciferase and plasmid expressing GAL4 DBD-fused CCPG or PGC-1α shown as a positive control. (E) HCT-116 cells were cotransfected with 300 ng of a native acyl-CoA oxidase (ACO) PPRE reporter plasmid, 50 ng of PPARγ, and 50 ng of CCPG or empty vector plasmids supplemented with Tro (1.0 µM). (F) MCF-7 cells were cotransfected with 300 ng of ER reporter pERE-TK-LUC and 25 ng of CCPG or empty vector plasmid in the presence of 17β-estrodiol (100 nM) or vehicle (ethanol). All the firefly luciferase and Renilla luciferase activities were determined 18-24 hr after transfection. Data were normalized to Renilla luciferase activity derived from the internal control plasmid phR-TK. Values were expressed relative to activation of empty vector and each value was derived from at least three independent experiments. Statistical analysis was done vs. the value from PPARγ alone in the presence of Tro using Student's t-test. (*): p<0.05.

Knowing that CCPG interacts with PPARγ, the inventor asked whether CCPG transactivates PPARγ. CCPG and PPARγ were co-expressed in HCT-116 cells with a consensus PPARγ-responsive luciferase reporter construct PPRE-TK-LUC (Zhu et al. (1996) Gene Expr 6, 185-195; Zhu et al. (1997) J Biol Chem 272, 25500-25506). A previously identified PPARγ coactivator PGC-1α was used as a positive control (Puigserver et al. (1998) Cell 92, 829-839). As indicated in FIG. 6A, CCPG alone did not activate the transcription of PPRE-TK-LUC, while in the presence of PPARγ and its ligand Tro (1.0 μM), CCPG significantly increased the transactivation of PPARγ in HCT-116 cells in a degree similar to PGC-1α. Interestingly, a moderate synergistic effect on the transactivation of PPARγ was observed when CCPG was co-transfected with PGC-1α. However, there was no direct interaction between CCPG and PGC-1α in co-IP assay (data not shown).

Figure 6C:
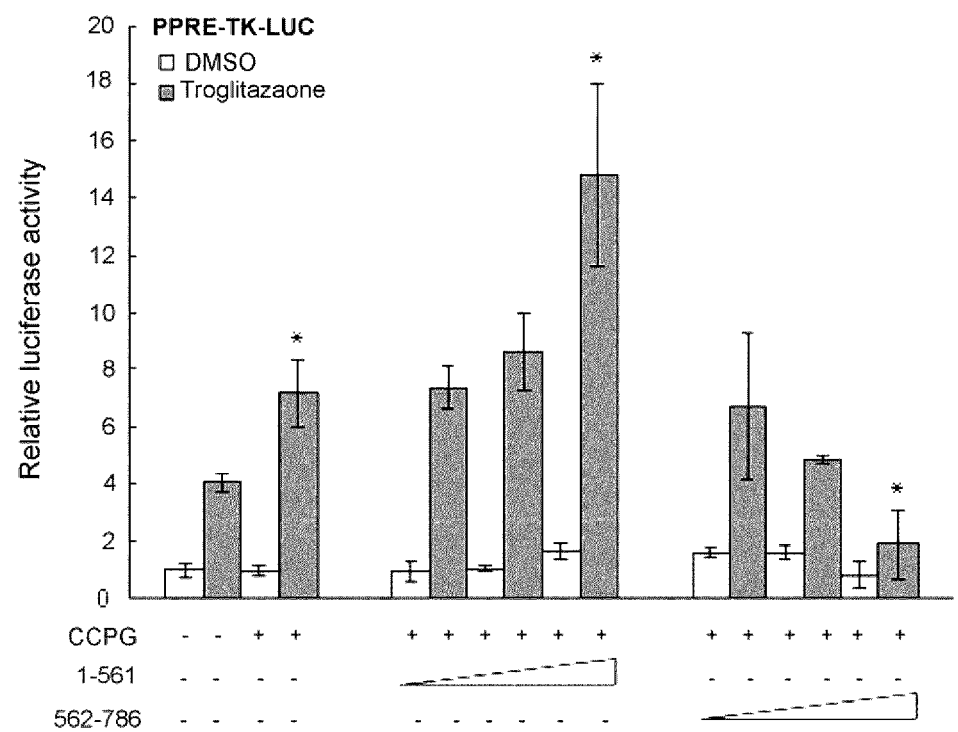
Figure 6D:
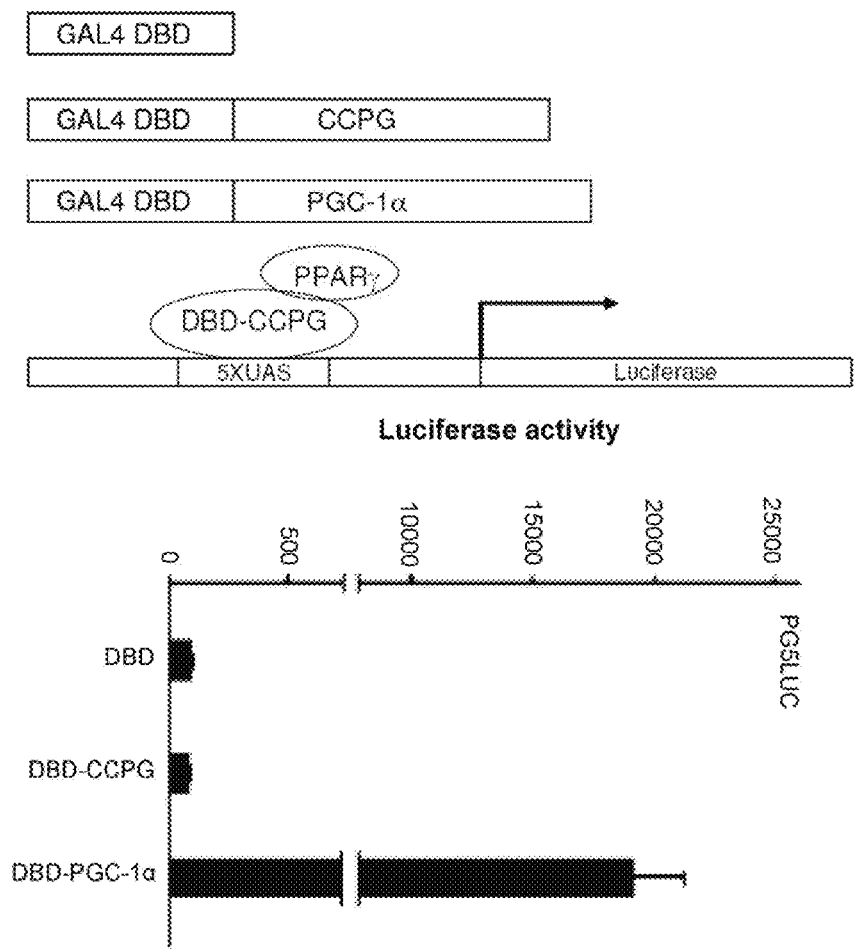
Figure 6:
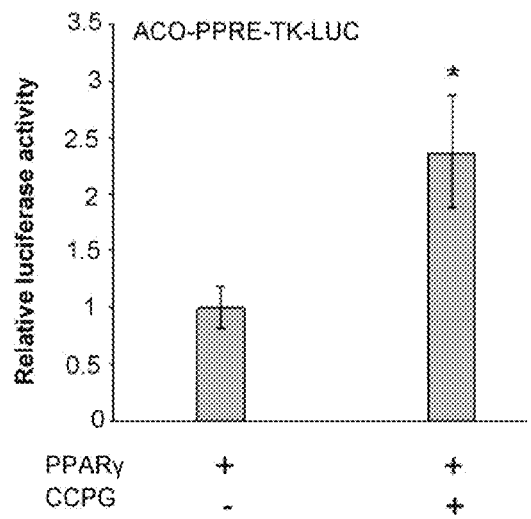
Figure 6:
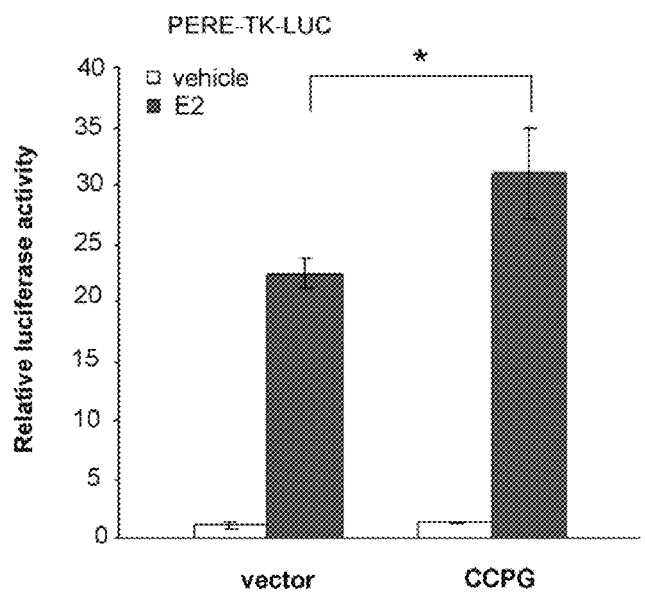

Given that N-terminal and C-terminal regions of CCPG are able to bind to PPARγ, the inventor subsequently dissected which region of CCPG mediated PPARγ transactivation. To avoid the interference of GFP in transactivation reporter assays, the inventor subcloned N-terminal CCPG (1-561) and C-terminal CCPG (562-786) into pcDNA3.1 expression vector. As shown in FIG. 6B, when cotransfected with equal amount of CCPG expression constructs, the N-terminus (1-561) had slightly higher ability to activate PPARγ, as compared with full-length CCPG. In contrast, C-terminus (562-786) had no ability to coactivate PPARγ and instead showed a suppressive effect on PPARγ activation. To evaluate whether either of these CCPG truncates suppresses wild-type CCPG activity, full-length CCPG was co-transfected with increasing quantities of either its N-terminus (1-561) or C-terminus (562-786) of CCPG expression constructs. Co-expression of CCPG and its N-terminus (1-561) generated synergistic effects on PPARγ transactivation in a dose-dependent manner, while co-expression of CCPG and its C-terminus (562-786) resulted in a dose-dependent inhibition of PPARγ activation indicating that the N-terminus of CCPG may have an activation domain (FIG. 6C). To test whether CCPG bears intrinsic transcriptional activity, as does by many coactivators such as PGC-1α (Puigserver et al. (1999) Science 286, 1368-1371), CCPG was fused to GAL4 DNA binding domain (GAL4 DBD). Transcriptional activity was analyzed through a luciferase reporter containing five GAL binding sites. As shown in FIG. 6D, CCPG fused to GAL4 DBD did not activate transcription while a strong transcriptional activity was seen with GAL4 DBD-fused PGC-1α. Thus, CCPG does not possess intrinsic transcriptional activity. Furthermore, cotransfection assay showed that CCPG coactivated PPARγ transactivation (FIG. 6E) when using a native acyl-CoA Oxidase (ACO) PPRE luciferase reporter (Park et al. (2003) Diabetologia 46, 365-377). In addition, ERE-reporter assay also demonstrated that CCPG moderately coactivates endogenous ERα in MCF-7 cells (FIG. 6F) in a ligand dependent manner.

Example 8

CCPG Promotes Adipogenesis of OP9 Preadipocytes

Given that CCPG augments the transactivation of PPARγ, the inventor investigated whether CCPG promotes adipogenesis of OP9 preadipocytes, a model for adipogenesis (Wolins et al. (2006) J. Lipid Res. 47, 450-460). The inventor initially examined the expression profiles of CCPG and PPARγ in differentiating OP9 cells. OP9 preadipocytes were stimulated to enter an adipocyte differentiation process with an adipogenic mix cocktail, and subjected to time-course sampling (Wolins et al. (2006) J. Lipid Res. 47, 450-460). Two days after reaching confluency (day 0), OP9 preadipocytes were transduced with adenoviruses Ad-GFP or Ad-GFP-CCPG (5 multiplicity of infection/cell) and cultured in MEM-α plus 10 percent BSA supplemented with or without adipogenic mix cocktail for further culture for up to 8 days. The culture media were refreshed every 2 days. At the specified time point, the morphological changes of the cells were photographed, and the cells were collected either for real-time RT-PCR or northern and western blot analyses. In addition, Oil-Red O staining was performed for the accumulated lipids in the adipocytes (Castillo et al. (1999) EMBO J 18, 3676-3687).

Figure 7:
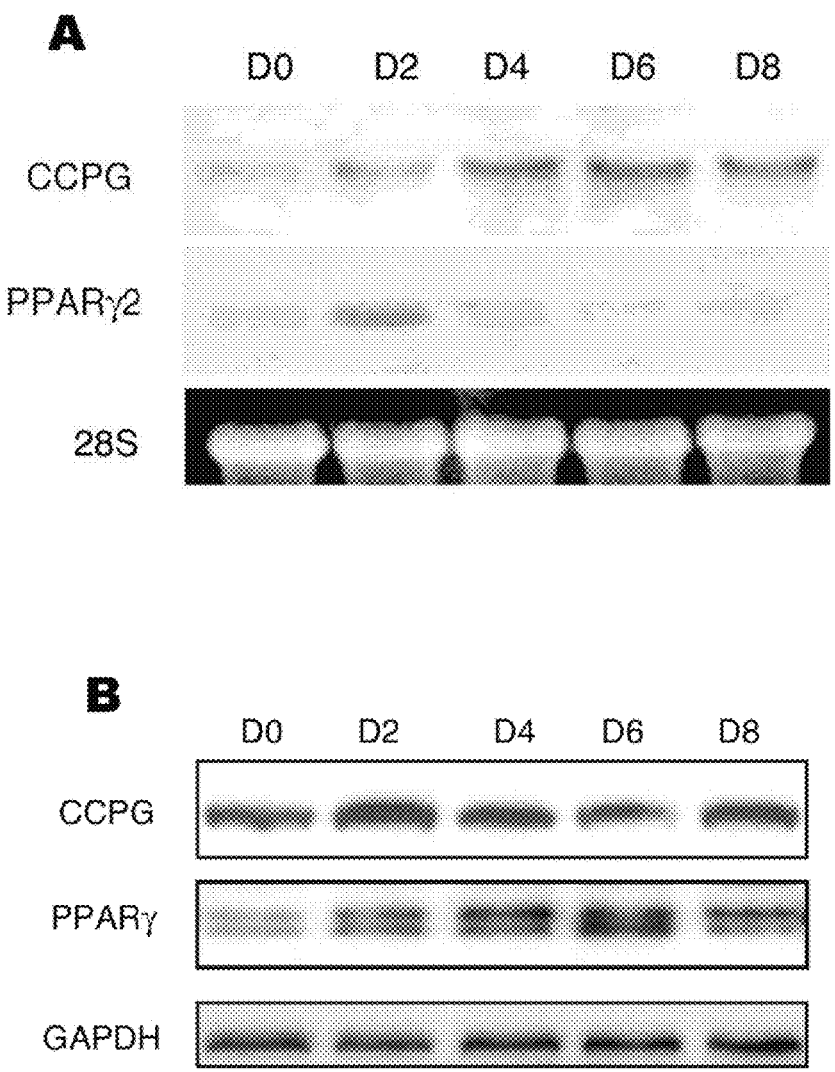
FIG. 7 illustrates the upregulation of CCPG expression and how CCPG interacts with endogenous PPARγ in differentiating OP9 cells during adipogenesis. (A) 10 µg of total RNAs were isolated on different dates from OP9 cells subjected to adipocyte differentiation-induced by adipogenic mix cocktail and hybridized with DIG-labeled CCPG probe. After stripping, membrane was rehybridized with DIG-labeled PPARγ 2 probe. Ethidium bromide (EtBr) stained 28S RNA was used as loading control. (B) Western blot of CCPG and PPARγ during adipogenesis as in (A). (C) OP9 preadipocytes were subjected to an adipogenic mix cocktail stimulation, meanwhile infected with adenovirus expressing GFP or GFP-CCPG fusion proteins. On differentiation day 2, cells were lysised for Co-IP assay. Anti-GFP monoclonal antibody was used to co-immunopreciptiate GFP and GFP fusion protein, and anti-PPARγ antibody was used to detect the interaction.
Figure 7C:
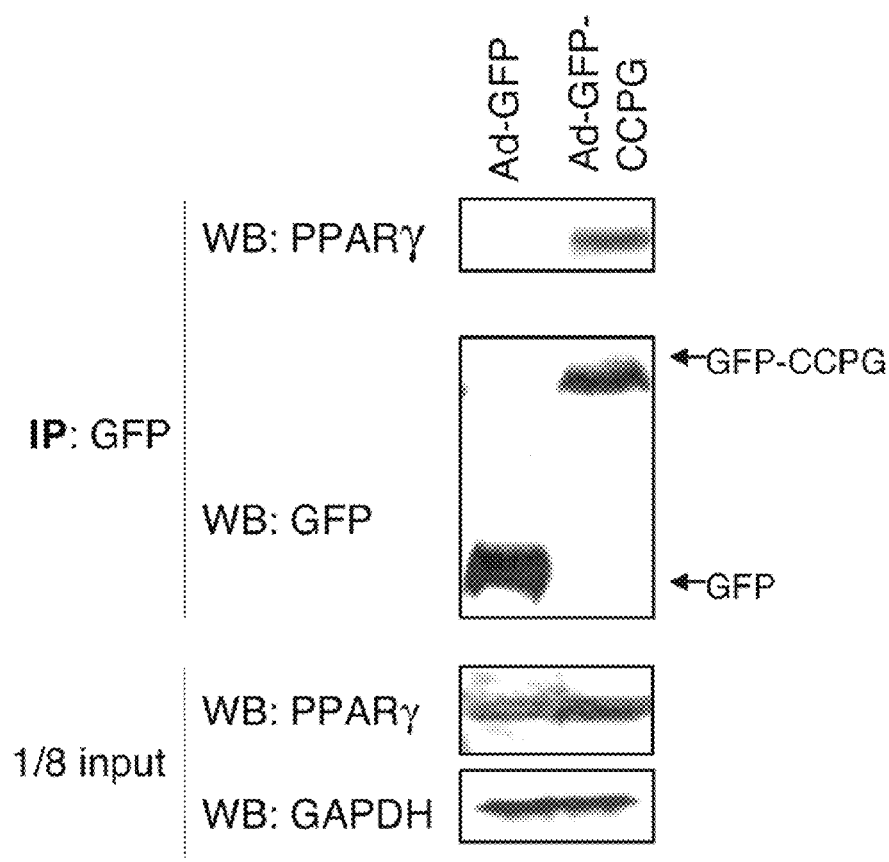
Figure 8:
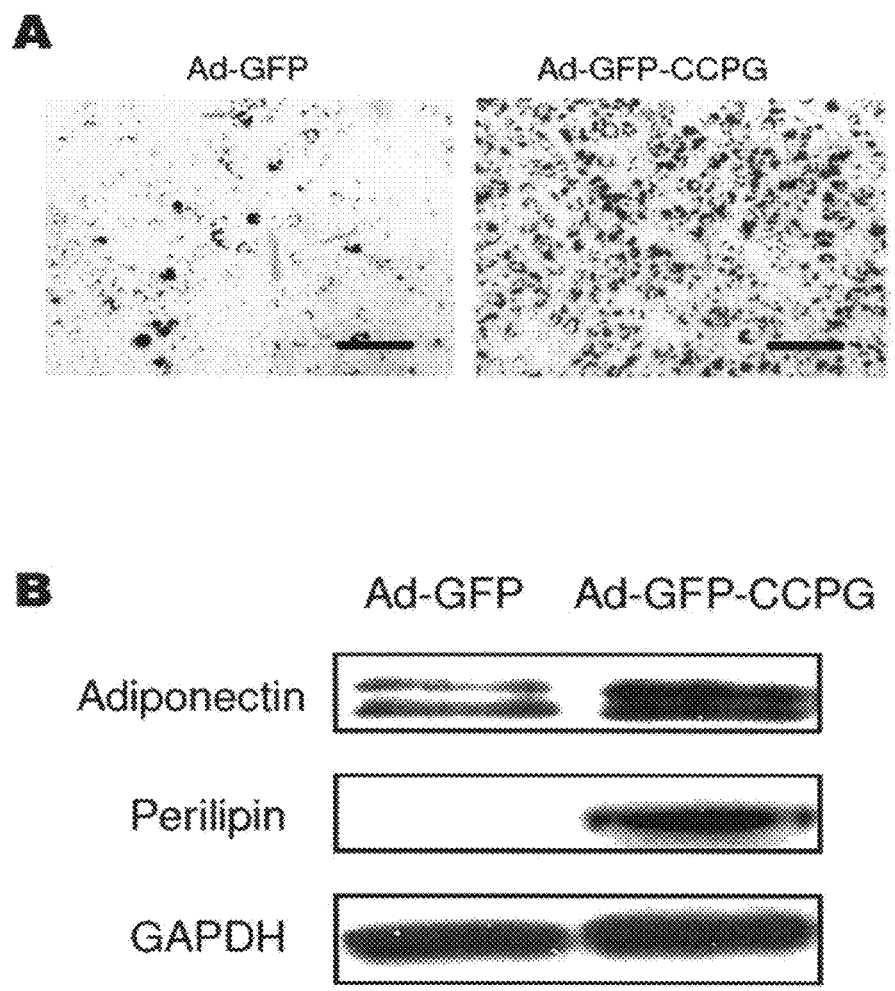
FIG. 8 illustrates CCPG promotion of adipogenesis of OP9 preadipocytes. (A) OP9 preadipocytes were transduced with an adenovirus expressing either GFP (Ad-GFP) or CCPG fused to GFP (Ad-GFP-CCPG). The resulting cells were subjected to a standard differentiation for 4 days with 1/10 concentration of the standard adipogenic mix cocktail in the media. Cells were fixed and stained with Oil-Red-O for microscopic examination and photographed at 400× magnification. There are many positive cells (red) in OP9 cells treated with Ad-GFP-CCPG. (B) Western blots for Adiponectin and perilipin protein in OP9 cells treated with either Ad-GFP or AD-GFP-CCPG for 4 days. (C) In another set of experiments, total RNAs were extracted from the cells and subjected to real time RT-PCR analysis. Adenoviral-CCPG RNAi was used to knockdown CCPG transcripts and LacZ RNAi was used as control. (D) Oil Red O staining of OP9 cells treated with only adipogenic mix cocktail (Control: CTL), Ad-LacZ RNAi or Ad-CCPG RNAi1, Ad-CCPG RNAi2 and Ad-CCPG RNAi2 mutation (RNAi2M) for 4 days. (E) Western blot analyses for CCPG, adiponectin, perilipin, and GAPDH in OP9 cells treated for 4 days. Scale bars: 30 µm.

As shown by Northern and western blots, CCPG mRNA transcription is up-regulated in OP9 cells starting from day 2 and peaking at day 4 during adipogenesis, whereas PPARγ mRNA transcription reached peak on day 2, then declined (FIG. 7A). The protein changes of CCPG had the similar pattern as its mRNA and PPARγ was increased until day 6 (FIG. 7B). To clarify whether CCPG interacts with endogenous PPARγ in differentiating OP9 cells, GFP and GFP-tagged CCPG were constructed in an adenovirus expression vector and the resulting viruses (designated as Ad-GFP or Ad-GFP-CCPG) were used to transduce OP9 preadipocytes subjected to adipocyte differentiation with stimulation of adipogenic mix cocktail. On adipocyte differentiation day 2, OP9 cells were collected and subjected to co-IP assay. As showed in FIG. 7C, CCPG interacts with endogenous PPARγ in differentiating OP9 cells. The inventor further investigated whether CCPG promotes the adipogenesis of OP9 preadipocytes. OP9 preadipocytes were transduced with virus Ad-GFP or Ad-GFP-CCPG and then subjected to adipocyte differentiation. To avoid the overwhelming effects of adipogenesis-induced by high concentration of cAMP and insulin (Wolins et al. (2006) J. Lipid Res. 47, 450-460), which may overshadow the effects of CCPG, low concentration of exogenous PPAR agonists (Tro, 0.5 μM) and other adipogenic agents such as dexamethasone (0.1 μM) and 3-isobutyl-1-methylxanthine (IBMX, 50 μM) were added to OP9 cell culture medium. As shown in FIG. 8A, OP9 preadipocytes transduced with Ad-GFP have very few cells (less than 5 percent) showed morphological differentiation towards adipocytes, while OP9 preadipocytes transduced with Ad-GFP-CCPG had a marked morphological differentiation into adipocytes at day 4 (more than 90 percent, ascertained by Oil-Red-O staining for lipid deposition). This result was further validated by immunodetection of adipocyte-specific marker adiponectin and perilipin (FIG. 8B).

Example 9

Interference RNA

Figure 8C:
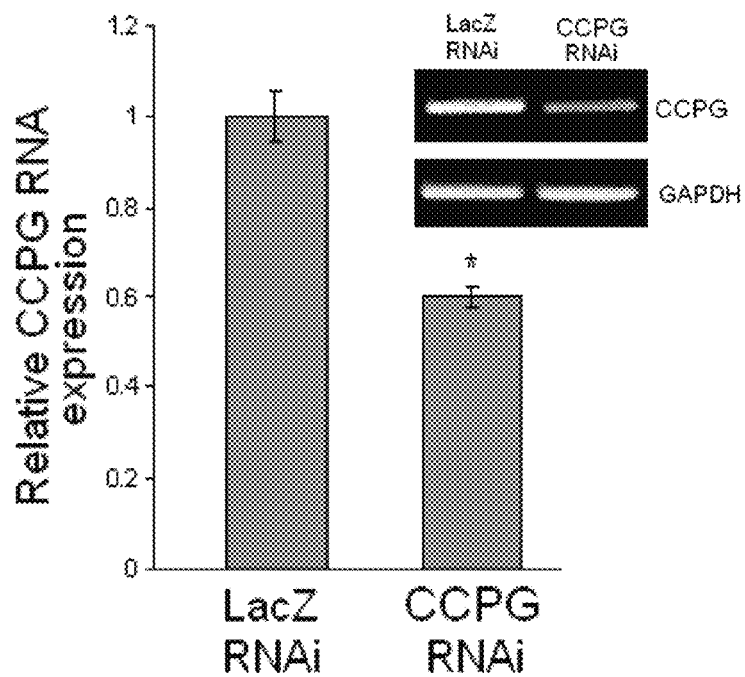
Figure 8:
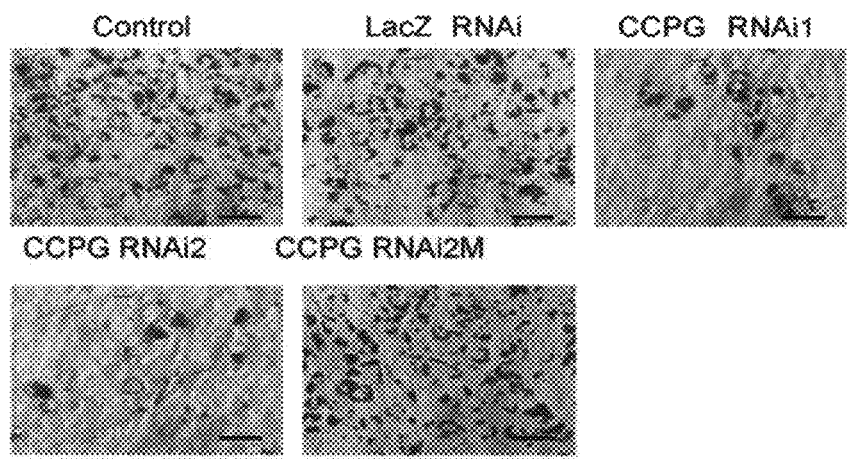
Figure 8:
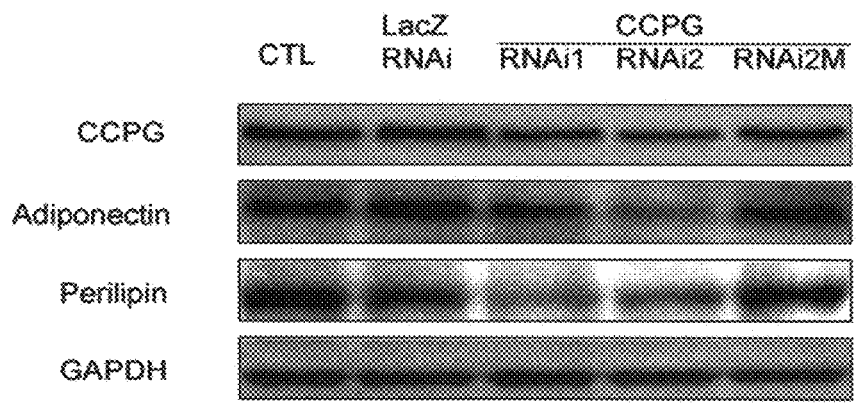

To evaluate the roles of endogenous CCPG in adipogenesis, CCPG transcripts were knocked down by adenovirus-delivered RNA interference (RNAi). OP9 preadipocytes were subjected to CCPG RNAi or control LacZ RNAi and adipogenesis with adipogenic mix cocktail for 4 days. Real-time RT-PCR showed that CCPG mRNA was significantly reduced in CCPG RNAi treated cells (FIG. 8C). Meanwhile, the adipocyte differentiation of OP9 cells was remarkably compromised in CCPG RNAi1 or CCPG RNAi2-treated OP9 cells, but not in LacZ RNAi and CCPG RNAi2 mutation (CCPG RNAi2M)-treated OP9 cells as examined by Oil-Red-O staining (FIG. 8D) and immunodetection of adipocyte-specific marker adiponectin and perilipin (FIG. 8E). Taken together, our data indicate that CCPG is a bona fide coactivator and promotes the adipogenic action of PPARγ.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed:

1. An isolated RNAi with sufficient complementarity to an RNA encoding a Constitutive Coactivator of PPARgamma polypeptide to inhibit expression of a nucleotide sequence encoding a Constitutive Coactivator of PPARgamma polypeptide.

2. The RNAi of claim 1, consisting of at least 10 contiguous nucleic acid residues of SEQ ID NO: 11, whereby the oligonucleotide reduces levels of Constitutive Coactivator of PPARgamma polypeptide.

3. The RNAi of claim 1, consisting of at least 20 contiguous nucleic acid residues of SEQ ID NO: 11, whereby the oligonucleotide reduces levels of Constitutive Coactivator of PPARgamma polypeptide.

4. The RNAi of claim 1, consisting of at least 30 contiguous nucleic acid residues of SEQ ID NO: 11, whereby the oligonucleotide reduces levels of Constitutive Coactivator of PPARgamma polypeptide.

5. The RNAi of claim 1, consisting of at least 40 contiguous nucleic acid residues of SEQ ID NO: 11, whereby the oligonucleotide reduces levels of Constitutive Coactivator of PPARgamma polypeptide.

6. The RNAi of claim 1, consisting of SEQ ID NO: 11, and conservatively modified variants thereof, whereby the oligonucleotide reduces levels of Constitutive Coactivator of PPARgamma polypeptide.

7. The RNAi of claim 1, consisting of SEQ ID NO: 11.

8. The RNAi of claim 1, consisting of at least 10 contiguous nucleic acid residues of SEQ ID NO: 12, whereby the oligonucleotide reduces levels of Constitutive Coactivator of PPARgamma polypeptide.

9. The RNAi of claim 1, consisting of at least 20 contiguous nucleic acid residues of SEQ ID NO: 12, whereby the oligonucleotide reduces levels of Constitutive Coactivator of PPARgamma polypeptide.

10. The RNAi of claim 1, consisting of at least 30 contiguous nucleic acid residues of SEQ ID NO: 12, whereby the oligonucleotide reduces levels of Constitutive Coactivator of PPARgamma polypeptide.

11. The RNAi of claim 1, consisting of at least 40 contiguous nucleic acid residues of SEQ ID NO: 12, whereby the oligonucleotide reduces levels of Constitutive Coactivator of PPARgamma polypeptide.

12. The RNAi of claim 1, consisting of SEQ ID NO: 12, and conservatively modified variants thereof, whereby the oligonucleotide reduces levels of Constitutive Coactivator of PPARgamma polypeptide.

13. The RNAi of claim 1, consisting of a nucleic acid sequence set forth in SEQ ID NO: 12.

14. The isolated RNAi of claim 1, further comprising a pharmaceutical formulation.

15. The isolated RNAi of claim 1, further comprising a gene delivery system selected from the group consisting of cells, liposomes, liposome-derived systems, and artificial viral envelopes.

16. The isolated RNAi of claim 1, further comprising an expression vector, the RNAi operably linked to control elements of the expression vector, and the expression vector selected from the group consisting of a plasmid, retrovirus, lentiviruses, adenovirus, parvoviruses, and an adeno-associated virus herpes simplex virus.

17. The isolated RNAi of claim 1, further comprising an adenovirus, the RNAi operably linked to control elements of the adenovirus.

18. A method of reducing adipogenesis in a mammal cell, comprising administering the composition of claim 17 to the mammal cell.

19. A method of reducing adipogenesis in a mammal cell in vivo, comprising, injecting intravenously, intramuscularly, or subcutaneously, an isolated RNAi with sufficient complementarity to an RNA encoding a Constitutive Coactivator of PPARgamma polypeptide to inhibit ex ession of a nucleotide sequence encoding a Constitutive Coactivator of PPAR-gamma polypeptide and an adenovirus, the RNAi operably linked to control elements of the adenovirus.

20. A method of reducing adipogenesis in a mammal cell, in vivo comprising, administering through topical application or direct application to tissue exposed through surgery, an isolated RNAi with sufficient complementarity to an RNA encoding a Constitutive Coactivator of PPARgamma polypeptide to inhibit expression of a nucleotide sequence encoding a Constitutive Coactivator of PPARgamma of polypeptide and an adenovirus, the RNAi operably linked to control elements of the adenovirus.

* * * * *

SEQUENCE LISTING

<160> NUMBER OF SEQ ID NOS: 21

<210> SEQ ID NO 1
<211> LENGTH: 786
<212> TYPE: PRT
<213> ORGANISM: Mus musculus

<400> SEQUENCE: 1

```
Met Gly Val Arg Gly Leu Gln Gly Phe Val Gly Ser Thr Cys Pro His
1               5                   10                  15

Ile Cys Thr Ile Val Asn Ile His Glu Leu Ala Glu Arg His Arg Asn
            20                  25                  30

Lys Tyr Pro Gly Cys Thr Pro Thr Ile Val Val Asp Ala Met Cys Cys
        35                  40                  45

Leu Arg Tyr Trp Tyr Thr Ala Glu Ser Trp Val Cys Gly Gly Gln Trp
    50                  55                  60

Arg Glu Tyr Tyr Cys Ala Leu Arg Asn Phe Val Ala Ala Phe Thr Ser
65                  70                  75                  80

Ala Gly Ile Lys Leu Ile Phe Phe Asp Gly Met Val Glu Pro Gly
                85                  90                  95

Lys Arg Asp Glu Trp Val Lys Arg Arg Leu Lys Asn Asn Arg Glu Ile
            100                 105                 110

Ser Lys Ile Phe His Tyr Ile Lys Ser Lys Arg Asp Gln Pro Gly Arg
        115                 120                 125

Asn Met Phe Phe Ile Pro Ser Gly Leu Ala Ile Phe Thr Arg Phe Ala
    130                 135                 140

Leu Lys Thr Leu Gly Gln Glu Thr Phe Cys Ser Leu Gln Glu Ala Asp
145                 150                 155                 160

Tyr Glu Val Ala Ser Tyr Gly Leu Gln His Asn Cys Leu Gly Ile Leu
                165                 170                 175

Gly Glu Asp Thr Asp Tyr Leu Ile Tyr Asp Thr Cys Pro Tyr Phe Ser
            180                 185                 190

Ile Gly Asp Leu Cys Leu Glu Ser Leu Gln Thr Ile Met Leu Cys Arg
        195                 200                 205

Glu Lys Leu Cys Glu Ser Leu Gly Leu Arg Val Ala Asp Leu Pro Leu
    210                 215                 220

Leu Ala Cys Leu Leu Gly Asn Asp Ile Thr Pro Glu Ser Met Phe Glu
225                 230                 235                 240
```

```
Ser Phe Arg Tyr Lys Cys Leu Ser Ser Tyr Ala Ser Val Lys Glu Asn
            245                 250                 255

Ala Gly Lys Lys Gly Asn Ile Ile Leu Ala Val Ser Asp Tyr Ile Ser
        260                 265                 270

Lys Val Leu His Leu Tyr Gln Gly Glu Lys Lys Ile Glu Glu Met Leu
            275                 280                 285

Pro Leu Gly Pro Asn Lys Ala Leu Phe Tyr Lys Gly Val Thr Ser Tyr
        290                 295                 300

Leu Leu Pro Gly Gln Lys Ser Pro Trp Leu Val Gln Lys Pro Lys Gly
305                 310                 315                 320

Met Ile Thr Asp Lys Gln Gln Met Val Ser Leu Asn Pro Glu Ser Lys
            325                 330                 335

Gln Glu Val Pro Met Cys Ile Asp Pro Glu Phe Lys Gln Glu Val Pro
            340                 345                 350

Val Cys Thr Asn Pro Glu Ser Met Gln Glu Val Pro Met Cys Met Asp
            355                 360                 365

Pro Glu Pro Asn Gln Glu Ala Ser Met Cys Thr Asp Pro Glu Ser Lys
            370                 375                 380

Gln Glu Val Pro Met Cys Thr Asp Ser Glu Ser Lys Pro Glu Val Ser
385                 390                 395                 400

Gln Tyr Thr Asn Pro Glu Ser Lys Gln Lys Leu Pro Ser Gly Ile Asp
            405                 410                 415

Thr Glu Phe Asn Leu Glu Ala Leu Met Cys Thr His Pro Glu Phe Lys
            420                 425                 430

Gln Glu Asp Val Met Asp Met Glu Pro Gly Ile Lys Gln Val Thr Met
            435                 440                 445

Val Ser Glu Ser Glu Ile Leu Lys Val Ala Arg Met His His Val His
450                 455                 460

Ser Glu Ser Tyr Leu Val Tyr Asn Ile Leu Ser Ser Gly Glu Ile Glu
465                 470                 475                 480

Cys Ser Asn Thr Leu Glu Asp Glu Leu Asp Gln Ala Leu Pro Ser Gln
            485                 490                 495

Ala Phe Ile Tyr Arg Pro Val Arg Gln Arg Val Tyr Ala Leu Leu Leu
            500                 505                 510

Gly Asp Trp Lys Asp Gly Ala Ser Thr Gly Pro Val Val Lys Glu Trp
            515                 520                 525

Phe Val Tyr Pro Gly Asn Ser Leu Lys His Pro Asp Leu Val Arg Pro
            530                 535                 540

Leu Gln Met Thr Val Gln Gly Gly Thr Pro Ser Leu Glu Val Leu Trp
545                 550                 555                 560

Leu Ser Gln Glu Pro Ala Val Gln Ala Gln Arg Leu Asp Thr Leu Leu
            565                 570                 575

Ala Cys Phe Asn Leu Ser Ser Ser Arg Glu Glu Leu Gln Ala Val Glu
            580                 585                 590

Ser Pro Leu Arg Ala Leu Cys Cys Leu Leu Ile Tyr Leu Phe Val Gln
            595                 600                 605

Val Asp Thr Leu Ser Leu Glu Asp Leu His Ala Phe Ile Ala Gln Ala
            610                 615                 620

Leu Cys Leu Gln Gly Lys Ser Thr Ser Gln Leu Met His Leu Gln Leu
625                 630                 635                 640

Asp Tyr Ile Asn Ser Arg Ala Val Gln Leu Gly Ser Leu Leu Val Arg
            645                 650                 655

Gly Leu Thr Thr Leu Val Leu Val Asn Ser Ala Cys Gly Phe Pro Trp
            660                 665                 670
```

```
Thr Thr Ser Glu Phe Met Pro Trp Asn Val Phe Asp Gly Lys Leu Phe
        675                 680                 685

His Gln Lys Tyr Leu Gln Ser Glu Lys Gly Tyr Ala Val Glu Val Leu
    690                 695                 700

Leu Glu Gln Asn Arg Ser Trp Leu Thr Lys Phe His Asn Leu Lys Ala
705                 710                 715                 720

Val Val Cys Lys Ala Cys Ser Lys Glu Asn Arg Arg Ile Val Gly Arg
                725                 730                 735

Thr His Trp Asp Ser Pro Tyr Thr Gly Arg Gln Gly Arg Gln Gly Tyr
                740                 745                 750

Ser Ser Tyr Arg Thr Asp Ser Thr His Gly His Ser Gly Gln Ser Trp
            755                 760                 765

Arg Asn Gln Gly Ser Gly Gly Arg Gln His Glu Arg Asn His Trp Arg
    770                 775                 780

Arg Tyr
785

<210> SEQ ID NO 2
<211> LENGTH: 910
<212> TYPE: PRT
<213> ORGANISM: Homo sapiens

<400> SEQUENCE: 2

Met Gly Val Arg Gly Leu Gln Gly Phe Val Gly Ser Thr Cys Pro His
1               5                   10                  15

Ile Cys Thr Val Val Asn Phe Lys Glu Leu Ala Glu His His Arg Ser
                20                  25                  30

Lys Tyr Pro Gly Cys Thr Pro Thr Ile Val Val Asp Ala Met Cys Cys
            35                  40                  45

Leu Arg Tyr Trp Tyr Thr Pro Glu Ser Trp Ile Cys Gly Gly Gln Trp
    50                  55                  60

Arg Glu Tyr Phe Ser Ala Leu Arg Asp Phe Val Lys Thr Phe Thr Ala
65                  70                  75                  80

Ala Gly Ile Lys Leu Ile Phe Phe Phe Asp Gly Met Val Glu Gln Asp
                85                  90                  95

Lys Arg Asp Glu Trp Val Lys Arg Arg Leu Lys Asn Asn Arg Glu Ile
            100                 105                 110

Ser Arg Ile Phe His Tyr Ile Lys Ser His Lys Glu Gln Pro Gly Arg
        115                 120                 125

Asn Met Phe Phe Ile Pro Ser Gly Leu Ala Val Phe Thr Arg Phe Ala
    130                 135                 140

Leu Lys Thr Leu Gly Gln Glu Thr Leu Cys Ser Leu Gln Glu Ala Asp
145                 150                 155                 160

Tyr Glu Val Ala Ser Tyr Gly Leu Gln His Asn Cys Leu Gly Ile Leu
                165                 170                 175

Gly Glu Asp Thr Asp Tyr Leu Ile Tyr Asp Thr Cys Pro Tyr Phe Ser
            180                 185                 190

Ile Ser Glu Leu Cys Leu Glu Ser Leu Asp Thr Val Met Leu Cys Arg
        195                 200                 205

Glu Lys Leu Cys Glu Ser Leu Gly Leu Cys Val Ala Asp Leu Pro Leu
    210                 215                 220

Leu Ala Cys Leu Leu Gly Asn Asp Ile Ile Pro Glu Gly Met Phe Glu
225                 230                 235                 240

Ser Phe Arg Tyr Lys Cys Leu Ser Ser Tyr Thr Ser Val Lys Glu Asn
                245                 250                 255
```

```
Phe Asp Lys Lys Gly Asn Ile Ile Leu Ala Val Ser Asp His Ile Ser
            260                 265                 270
Lys Val Leu Tyr Leu Tyr Gln Gly Glu Lys Leu Glu Glu Ile Leu
        275                 280                 285
Pro Leu Gly Pro Asn Lys Ala Leu Phe Tyr Lys Gly Met Ala Ser Tyr
290                 295                 300
Leu Leu Pro Gly Gln Lys Ser Pro Trp Phe Phe Gln Lys Pro Lys Gly
305                 310                 315                 320
Val Ile Thr Leu Asp Lys Gln Val Ile Ser Thr Ser Ser Asp Ala Glu
                325                 330                 335
Ser Arg Glu Glu Val Pro Met Cys Ser Asp Ala Glu Ser Arg Gln Glu
                340                 345                 350
Val Pro Met Cys Thr Gly Pro Glu Ser Arg Glu Val Pro Val Tyr
            355                 360                 365
Thr Asp Ser Glu Pro Arg Gln Glu Val Pro Met Cys Ser Asp Pro Glu
    370                 375                 380
Pro Arg Gln Glu Val Pro Thr Cys Thr Gly Pro Glu Ser Arg Arg Glu
385                 390                 395                 400
Val Pro Met Cys Ser Asp Pro Glu Pro Arg Gln Glu Val Pro Met Cys
                405                 410                 415
Thr Gly Pro Glu Ala Arg Gln Glu Val Pro Met Tyr Thr Asp Ser Glu
            420                 425                 430
Pro Arg Gln Glu Val Pro Met Tyr Thr Asp Ser Glu Pro Arg Gln Glu
    435                 440                 445
Val Pro Met Tyr Thr Gly Ser Glu Pro Arg Gln Glu Val Pro Met Tyr
        450                 455                 460
Thr Gly Pro Glu Ser Arg Gln Glu Val Pro Met Tyr Thr Gly Pro Glu
465                 470                 475                 480
Ser Arg Gln Glu Val Leu Ile Arg Thr Asp Pro Glu Ser Arg Gln Glu
                485                 490                 495
Ile Met Cys Thr Gly His Glu Ser Lys Gln Glu Val Pro Ile Cys Thr
            500                 505                 510
Asp Pro Ile Ser Lys Gln Glu Asp Ser Met Cys Thr His Ala Glu Ile
        515                 520                 525
Asn Gln Lys Leu Pro Val Ala Thr Asp Phe Glu Phe Lys Leu Glu Ala
    530                 535                 540
Leu Met Cys Thr Asn Pro Glu Ile Lys Gln Glu Asp Pro Thr Asn Val
545                 550                 555                 560
Gly Pro Glu Val Lys Gln Val Thr Met Val Ser Asp Thr Glu Ile
                565                 570                 575
Leu Lys Val Ala Arg Thr His His Val Gln Ala Glu Ser Tyr Leu Val
            580                 585                 590
Tyr Asn Ile Met Ser Ser Gly Glu Ile Glu Cys Ser Asn Thr Leu Glu
        595                 600                 605
Asp Glu Leu Asp Gln Ala Leu Pro Ser Gln Ala Phe Ile Tyr Arg Pro
    610                 615                 620
Ile Arg Gln Arg Val Tyr Ser Leu Leu Leu Glu Asp Cys Gln Asp Val
625                 630                 635                 640
Thr Ser Thr Cys Leu Ala Val Lys Glu Trp Phe Val Tyr Pro Gly Asn
                645                 650                 655
Pro Leu Arg His Pro Asp Leu Val Arg Pro Leu Gln Met Thr Ile Pro
            660                 665                 670
Gly Gly Thr Pro Ser Leu Lys Ile Leu Trp Leu Asn Gln Glu Pro Glu
```

```
              675                 680                 685
Ile Gln Val Arg Arg Leu Asp Thr Leu Leu Ala Cys Phe Asn Leu Ser
690                 695                 700

Ser Ser Arg Glu Glu Leu Gln Ala Val Glu Ser Pro Phe Gln Ala Leu
705                 710                 715                 720

Cys Cys Leu Leu Ile Tyr Leu Phe Val Gln Val Asp Thr Leu Cys Leu
                725                 730                 735

Glu Asp Leu His Ala Phe Ile Ala Gln Ala Leu Cys Leu Gln Gly Lys
                740                 745                 750

Ser Thr Ser Gln Leu Val Asn Leu Gln Pro Asp Tyr Ile Asn Pro Arg
            755                 760                 765

Ala Val Gln Leu Gly Ser Leu Val Arg Gly Leu Thr Thr Leu Val
            770                 775                 780

Leu Val Asn Ser Ala Cys Gly Phe Pro Trp Lys Thr Ser Asp Phe Met
785                 790                 795                 800

Pro Trp Asn Val Phe Asp Gly Lys Leu Phe His Gln Lys Tyr Leu Gln
                805                 810                 815

Ser Glu Lys Gly Tyr Ala Val Glu Val Leu Leu Glu Gln Asn Arg Ser
            820                 825                 830

Arg Leu Thr Lys Phe His Asn Leu Lys Ala Val Val Cys Lys Ala Cys
            835                 840                 845

Met Lys Glu Asn Arg Arg Ile Thr Gly Arg Ala His Trp Gly Ser His
850                 855                 860

His Ala Gly Arg Trp Gly Arg Gln Gly Ser Ser Tyr His Arg Thr Gly
865                 870                 875                 880

Ser Gly Tyr Ser Arg Ser Ser Gln Gly Gln Pro Trp Arg Asp Gln Gly
                885                 890                 895

Pro Gly Ser Arg Gln Tyr Glu His Asp Gln Trp Arg Arg Tyr
            900                 905                 910

<210> SEQ ID NO 3
<211> LENGTH: 785
<212> TYPE: PRT
<213> ORGANISM: Rattus norvegicus

<400> SEQUENCE: 3

Met Gly Val Arg Gly Leu Gln Gly Phe Val Gly Ser Thr Cys Pro His
1               5                   10                  15

Ile Cys Thr Thr Val Asn Leu His Glu Leu Ala Glu Ser His Arg Ala
                20                  25                  30

Lys Tyr Pro Gly Ser Thr Pro Thr Ile Val Val Asp Ala Met Cys Cys
            35                  40                  45

Leu Arg Tyr Trp Tyr Thr Ala Glu Ser Trp Val Cys Gly Gly Gln Trp
        50                  55                  60

Arg Glu Tyr Tyr Ser Ala Leu Arg Asp Phe Leu Ala Ala Phe Thr Ser
65                  70                  75                  80

Ala Gly Ile Lys Leu Ile Phe Phe Asp Gly Thr Val Glu Pro Gly
                85                  90                  95

Lys Arg Asp Glu Trp Val Lys Arg Arg Leu Lys Asn Asn Arg Glu Ile
            100                 105                 110

Ser Arg Ile Phe His Tyr Ile Lys Ser Lys Arg Glu Gln Pro Gly Arg
        115                 120                 125

Asn Met Phe Phe Ile Pro Ser Gly Leu Ala Ile Phe Thr Arg Phe Ala
    130                 135                 140

Leu Lys Ser Leu Gly Gln Glu Thr Phe Cys Ser Leu Gln Glu Ala Asp
```

-continued

```
            145                 150                 155                 160
Tyr Glu Val Ala Ser Tyr Gly Leu Gln His Asn Cys Leu Gly Ile Leu
                    165                 170                 175
Gly Glu Asp Thr Asp Tyr Leu Ile Tyr Asp Thr Cys Pro Tyr Leu Ser
                180                 185                 190
Ile Gly Asp Leu Cys Leu Glu Ser Leu Gln Thr Ile Leu Leu Cys Arg
            195                 200                 205
Glu Lys Leu Cys Glu Ser Leu Gly Leu Arg Val Ser Asp Leu Pro Leu
        210                 215                 220
Leu Ala Cys Leu Leu Gly Asn Asp Ile Thr Pro Glu Gly Met Phe Glu
225                 230                 235                 240
Ser Phe Arg Tyr Lys Cys Leu Ser Ser Tyr Ala Ser Val Lys Glu Asn
                245                 250                 255
Ala Gly Lys Lys Gly Asn Ile Ile Leu Ala Val Ser Asp Tyr Ile Ser
                260                 265                 270
Lys Val Leu His Leu Tyr Gln Gly Glu Lys Lys Ile Glu Glu Met Leu
            275                 280                 285
Pro Leu Gly Pro Asn Lys Ala Leu Phe Tyr Lys Gly Val Thr Ser Tyr
        290                 295                 300
Leu Leu Pro Gly Gln Lys Ser Pro Trp Leu Val Gln Lys Pro Lys Ser
305                 310                 315                 320
Ile Ile Thr Asp Lys Gln Met Ala Ser Leu Asn Pro Gly Ser Lys Gln
                325                 330                 335
Glu Val Pro Met Cys Ile Asp Pro Glu Phe Lys Gln Glu Val Pro Val
                340                 345                 350
Cys Thr Asn Pro Glu Ser Met Gln Glu Val Pro Met Cys Met Asp Pro
            355                 360                 365
Glu Pro Asn Gln Glu Ala Ser Val Cys Met Asp Arg Glu Ser Lys Pro
        370                 375                 380
Glu Val Pro Met Cys Thr Asp Pro Glu Ser Lys Pro Glu Val Pro Leu
385                 390                 395                 400
Tyr Thr Asn Pro Glu Ser Lys Gln Lys Ser Pro Ser Glu Ile Asp Pro
                405                 410                 415
Lys Cys Asn Leu Glu Ala Leu Thr Cys Thr Tyr Pro Glu Val Lys Gln
                420                 425                 430
Glu Asp Ala Met Asp Met Glu Pro Glu Ile Lys Gln Ala Thr Met Val
            435                 440                 445
Ser Glu Ser Glu Ile Leu Lys Val Ala Arg Met His His Val His Ser
        450                 455                 460
Glu Ser Tyr Leu Val Tyr Asn Ile Leu Ser Ser Gly Glu Ile Glu Cys
465                 470                 475                 480
Ser Asn Thr Leu Glu Asp Glu Leu Asp Gln Ala Leu Pro Ser Gln Ala
                485                 490                 495
Phe Ile Tyr Arg Pro Val Arg Gln Arg Val Tyr Ser Leu Leu Leu Glu
                500                 505                 510
Asp Trp Lys Asp Gly Ala Ser Thr Gly Pro Val Val Lys Glu Trp Phe
            515                 520                 525
Val Tyr Pro Gly Asn Ser Leu Lys His Pro Asp Leu Val Arg Pro Leu
        530                 535                 540
Gln Met Thr Val Gln Gly Gly Thr Pro Ser Leu Glu Val Leu Trp Leu
545                 550                 555                 560
Ser Gln Glu Pro Ala Ala Gln Ala Arg Arg Leu Asp Thr Leu Leu Ala
                565                 570                 575
```

-continued

```
Cys Phe Asn Leu Ser Ser Ser Arg Glu Glu Leu Gln Ser Val Glu Ser
            580                 585                 590

Pro Leu Arg Ala Leu Cys Cys Leu Ile Tyr Leu Phe Val Gln Val
        595                 600                 605

Asp Thr Leu Ser Leu Glu Asp Leu His Ala Phe Ile Ala Gln Ala Leu
        610                 615                 620

Cys Leu Gln Gly Lys Ser Thr Ser Gln Leu Met His Leu Gln Leu Asp
625                 630                 635                 640

Tyr Ile Asn Ser Arg Ala Val Gln Leu Gly Ser Leu Val Arg Gly
                645                 650                 655

Leu Thr Thr Leu Val Leu Val Asn Ser Ala Cys Gly Phe Pro Trp Thr
        660                 665                 670

Thr Ser Asp Phe Met Pro Trp Asn Val Phe Asp Gly Lys Leu Phe His
        675                 680                 685

Gln Lys Tyr Leu Gln Ser Glu Lys Gly Tyr Gly Val Glu Thr Leu Leu
        690                 695                 700

Glu Gln Asn Arg Ser Trp Leu Thr Thr Phe His Asn Leu Lys Ala Val
705                 710                 715                 720

Val Cys Lys Ala Cys Ser Lys Glu Asn Arg Arg Ile Val Gly Arg Ile
                725                 730                 735

His Trp Asn Ser His Tyr Thr Gly Arg Gln Gly Arg Gln Gly His Gly
                740                 745                 750

Ser Tyr Arg Ser Gly Ser Thr His Gly His Ser Gly Gln Ser Trp Arg
        755                 760                 765

Asp Gln Gly Ser Gly Gly Arg Gln His Glu His Asp Trp Arg Arg
        770                 775                 780

Tyr
785

<210> SEQ ID NO 4
<211> LENGTH: 782
<212> TYPE: PRT
<213> ORGANISM: Canis lupus

<400> SEQUENCE: 4

Met Gly Val Arg Gly Leu Gln Gly Phe Val Gly Ser Thr Cys Pro His
1               5                   10                  15

Ile Cys Thr Val Val Asn Phe Lys Glu Leu Ala Glu His His Arg Asn
                20                  25                  30

Gln His Pro Gly Cys Thr Pro Thr Ile Val Val Asp Ala Met Cys Cys
        35                  40                  45

Leu Arg Tyr Trp Tyr Thr Pro Glu Ser Trp Ile Cys Gly Gly Gln Trp
    50                  55                  60

Arg Glu Tyr Phe Ser Ser Leu Arg Asp Phe Val Lys Thr Phe Thr Thr
65                  70                  75                  80

Val Gly Ile Lys Leu Ile Phe Phe Asp Gly Met Val Glu Gln Glu
                85                  90                  95

Lys Arg Asp Glu Trp Val Lys Arg Leu Lys Asn Asn Arg Glu Ile
        100                 105                 110

Ser Arg Ile Phe His Tyr Ile Lys Ser His Lys Glu Gln Pro Gly Arg
        115                 120                 125

Asn Met Phe Phe Ile Pro Ser Gly Leu Ala Ile Phe Thr Arg Phe Ala
    130                 135                 140

Leu Lys Ala Leu Gly Gln Glu Thr Leu Cys Ser Leu Gln Glu Ala Asp
145                 150                 155                 160
```

-continued

```
Tyr Glu Val Ala Ser Tyr Gly Phe Gln Asn Asn Cys Leu Gly Ile Leu
                165                 170                 175
Gly Glu Asp Thr Asp Tyr Leu Ile Tyr Asp Thr Cys Pro Tyr Phe Ser
            180                 185                 190
Ile Gly Asp Leu Cys Leu Glu Ser Leu Ser Thr Val Met Leu Cys Arg
        195                 200                 205
Lys Lys Leu Cys Glu Ser Leu Asn Ile Asn Val Ala Asp Leu Pro Leu
    210                 215                 220
Leu Ala Cys Leu Leu Gly Asn Asp Ile Ile Pro Glu Gly Met Phe Glu
225                 230                 235                 240
Ser Phe Arg Tyr Lys Cys Leu Ser Ser Tyr Thr Ser Val Lys Glu Asn
                245                 250                 255
Phe Asp Lys Lys Gly Asn Ile Ile Leu Ala Val Ala Asp His Ile Ser
            260                 265                 270
Lys Val Leu His Ser His Gln Gly Glu Lys Lys Leu Glu Asp Met Leu
        275                 280                 285
Pro Leu Gly Pro Asn Lys Ala Leu Phe Tyr Lys Gly Val Ala Ser Tyr
    290                 295                 300
Leu Leu Pro Gly Gln Lys Ser Pro Trp Phe Phe Gln Lys Pro Lys Ser
305                 310                 315                 320
Leu Ile Ser Leu Gly Lys Gln Val Val Ser Met Asn Pro Glu Ser Lys
                325                 330                 335
Gln Glu Val Pro Met Cys Thr Glu Pro Glu Ser Lys Gln Glu Val Pro
            340                 345                 350
Met Cys Thr Pro Pro Glu Ser Arg Gln Gly Val Pro Met Cys Thr Asp
        355                 360                 365
Pro Glu Ser Arg Gln Gly Val Pro Val Cys Thr Asp Pro Glu Ser Arg
    370                 375                 380
Gln Gly Val Pro Met Cys Thr Asp Pro Glu Ser Arg Gln Gly Val Ser
385                 390                 395                 400
Met Cys Thr Asp Pro Glu Ser Lys Gln Gly Gln Lys Leu Pro Pro Gly
                405                 410                 415
Ala Asp Pro Glu Phe Lys Leu Glu Ala Leu Met Cys Thr Asn Pro Ala
            420                 425                 430
Ile Lys Glu Asp Leu Val Asn Met Glu Pro Glu Val Lys Gln Val Thr
        435                 440                 445
Leu Val Ser Asp Pro Asp Ile Leu Lys Val Ala Arg Ala Asp His Val
    450                 455                 460
Gln Ala Glu Ser Tyr Leu Val Tyr Asn Ile Met Ser Ser Gly Glu Ile
465                 470                 475                 480
Glu Cys Ser Asn Thr Leu Glu Asp Ala Leu Asp Gln Ala Leu Pro Ser
                485                 490                 495
Gln Ala Phe Val Tyr Arg Pro Val Arg Gln Arg Val Tyr Ser Leu Leu
            500                 505                 510
Leu Gly Asp Gly Gly Asp Gly Ala Gly Thr Cys Pro Thr Val Lys Glu
        515                 520                 525
Trp Phe Val Tyr Ser Gly Asn Pro Leu Arg His Pro Asp Leu Val Arg
    530                 535                 540
Pro Leu Gln Met Asn Ile Pro Gly Gly Thr Pro Asn Leu Lys Leu Leu
545                 550                 555                 560
Trp Leu Asn Gln Glu Pro Gly Thr Gln Ala Arg Arg Val Glu Ala Leu
                565                 570                 575
Leu Gly Cys Phe Asp Leu Ser Ser Arg Glu Glu Leu Gln Ala Val
            580                 585                 590
```

```
Glu Asn Pro Phe Arg Ala Leu Cys Cys Leu Leu Thr Tyr Leu Phe Val
        595                 600                 605

Gln Val Asp Thr Leu Cys Leu Glu Asp Leu His Ala Phe Ile Ala Gln
610                 615                 620

Ala Leu Cys Leu Gln Gly Lys Ser Thr Val Gln Leu Val Asp Leu Gln
625                 630                 635                 640

Leu Asp Tyr Ile Asp Ser Arg Ala Val Gln Leu Gly Ser Leu Leu Val
            645                 650                 655

Arg Gly Leu Thr Thr Leu Val Leu Val Asn Ser Ala Cys Gly Phe Pro
            660                 665                 670

Trp Arg Thr Ser Asp Phe Met Pro Trp Asn Val Phe Asp Gly Lys Leu
            675                 680                 685

Phe His Gln Lys Tyr Leu Gln Ser Glu Lys Gly Tyr Ala Val Glu Ala
        690                 695                 700

Leu Val Glu His Asn Arg Ser Arg Leu Thr Arg Phe His Ala Leu Lys
705                 710                 715                 720

Ser Val Val Cys Lys Ala Cys Ala Lys Glu Asn Arg Arg Ile Val Ser
                725                 730                 735

Arg Gln His Trp Arg Ser His Gln Pro Gly Gly His His Gly Ala Gln
            740                 745                 750

Ala Arg Gly Arg Glu Val Leu Gly Pro Gln Ser Leu Ser Thr Ala Gly
            755                 760                 765

Asp Glu Pro Met Thr Asp Gln Gly Pro Cys Phe Gly Val Ala
            770                 775                 780

<210> SEQ ID NO 5
<211> LENGTH: 770
<212> TYPE: PRT
<213> ORGANISM: Bos taurus

<400> SEQUENCE: 5

Met Ala Glu Ser Val Gly Gly Arg Gly Gly Arg Leu Glu Pro Ala His
1               5                   10                  15

Leu Arg Ala Ser Leu Arg Ala Trp Arg Leu Gly Pro Gln Ala Pro His
            20                  25                  30

Gly Arg Gly Arg Ser Arg Ser Pro Phe Thr Ala Glu Lys Glu Ser Asp
        35                  40                  45

Ser Arg Trp Ile Leu Pro Arg Ser Ser Ile Met Gly Val Arg Gly Leu
    50                  55                  60

His Gly Phe Val Ala Ser Ser Cys Pro His Val Cys Thr Val Val Asn
65                  70                  75                  80

Phe Lys Glu Leu Ala Glu Arg His Arg Ser Gln His Pro Gly Gly Thr
                85                  90                  95

Pro Thr Ile Val Val Asp Ala Met Cys Cys Leu Arg Tyr Trp Tyr Thr
            100                 105                 110

Pro Glu Ser Trp Val Cys Gly Gly Gln Trp Arg Glu Tyr Tyr Ser Ser
        115                 120                 125

Leu Arg Glu Phe Val Arg Thr Phe Thr Ala Val Gly Ile Lys Leu Ile
    130                 135                 140

Phe Phe Phe Asp Gly Met Val Glu Gln Ser Lys Arg Asp Glu Trp Val
145                 150                 155                 160

Lys Arg Arg Leu Lys Asn Asn Arg Glu Ile Ala Lys Ile Phe His Tyr
                165                 170                 175

Ile Lys Ser Arg Arg Glu Gln Pro Gly Arg Asn Met Phe Phe Ile Pro
            180                 185                 190
```

Ser Gly Leu Ala Ile Phe Thr Arg Phe Ala Leu Lys Ala Leu Gly Gln
            195                 200                 205

Glu Thr Leu Cys Ser Leu Gln Glu Ala Asp Tyr Glu Val Ala Ser Tyr
        210                 215                 220

Gly Phe Gln Asn Asn Cys Leu Gly Ile Leu Gly Glu Asp Thr Asp Tyr
225                 230                 235                 240

Leu Ile Tyr Asp Thr Cys Pro Tyr Phe Ser Ile Ser Glu Leu Ser Leu
            245                 250                 255

Asp Ser Leu Asp Thr Val Met Leu Cys Arg Glu Lys Leu Cys Gln Ser
        260                 265                 270

Leu Gly Leu His Leu Ala Asp Leu Pro Leu Leu Ala Cys Leu Leu Gly
    275                 280                 285

Asn Asp Val Ile Pro Glu Gly Met Phe Glu Ser Phe Arg Tyr Lys Cys
290                 295                 300

Leu Thr Ser Tyr Ala Ser Val Arg Glu Ser Cys Asp Arg Lys Gly Asn
305                 310                 315                 320

Val Ile Leu Ala Val Ala Glu His Ile Ser Lys Val Leu Arg Leu His
            325                 330                 335

Gln Gly Glu Lys Lys Leu Glu Glu Met Leu Pro Leu Gly Pro Asn Lys
        340                 345                 350

Ala Leu Phe Tyr Lys Gly Val Ala Ser Tyr Leu Leu Pro Gly Gln Lys
    355                 360                 365

Ser Pro Trp Phe Ile Gln Lys Pro Glu Asp Val Val Thr Leu Asp Lys
370                 375                 380

Gln Val Leu Ser Met Ser Ser Asp Pro Glu Ser Lys Gln Glu Phe Pro
385                 390                 395                 400

Val Cys Met Asp Ser Glu Ser Lys Gln Lys Leu Pro Val Gly Thr Asp
            405                 410                 415

Pro Glu Phe Asn Leu Glu Ala Pro Met Cys Thr Asn Thr Glu Val Lys
        420                 425                 430

Gln Glu Asp Pro Val Asn Val Gly Pro Glu Ala Lys His Gln Val Thr
    435                 440                 445

Val Val Leu Asp Pro Glu Ile Leu Lys Val Gly Gly His Ala His Pro
450                 455                 460

Asn Thr Thr Gln Ser Leu Asp Gly Gly Leu Glu Ala Asp Leu His Val
465                 470                 475                 480

Glu Val Pro Thr Ser Met Gln Pro Glu Glu Lys Gly Glu Gln Arg Gln
            485                 490                 495

Asp Arg Gly Pro Ser Leu Arg Leu Ala Ser Met Leu Ser Val Thr His
        500                 505                 510

Val His Arg Val Ser Asp Ala Ile Gln Pro Ser His Pro Leu Asn Lys
    515                 520                 525

Leu His Leu Ile Val Gly Gln Val Ala Arg Ala Gln His Val Gln Ala
    530                 535                 540

Glu Ser Tyr Leu Val Tyr Ser Val Met Ser Ser Gly Glu Val Glu Cys
545                 550                 555                 560

Ser Asn Ser Leu Glu Asp Ala Thr Asp Gln Ala Leu Pro Ser Gln Ala
            565                 570                 575

Phe Val Tyr Arg Pro Val Arg Gln Arg Val Tyr Ser Leu Leu Leu Gly
        580                 585                 590

Gly Gly Gly Gly Ser Ser Thr Gly Pro Ala Val Lys Glu Trp Phe
    595                 600                 605

Val Tyr Ser Gly Asn Pro Leu Arg Gln Pro Asp Leu Val Arg Pro Leu

|  |  |  |  |  |  |  |  |  |  |
|---|---|---|---|---|---|---|---|---|---|
| Gln | Met | Asn | Ile | Pro | Gly | Gly | Thr | Pro | Ser | Leu | Arg | Gln | Leu | Trp | Leu |
| 625 |  |  |  |  | 630 |  |  |  | 635 |  |  |  |  |  | 640 |

```
            610                 615                 620

Gln Met Asn Ile Pro Gly Gly Thr Pro Ser Leu Arg Gln Leu Trp Leu
625                 630                 635                 640

Ser Gln Glu Pro Gly Ile Gln Ala Gln Arg Leu Asp Thr Leu Leu Ala
                645                 650                 655

Cys Phe Asp Leu Ser Ser Arg Glu Glu Leu Gln Ala Val Glu Arg
            660                 665                 670

Pro Phe Gln Ala Leu Cys Cys Leu Leu Val Tyr Leu Phe Val Gln Val
                675                 680                 685

Lys His Lys Ser Asp Leu Gly Trp Glu Gln Thr Ala Gln Arg Arg Ala
            690                 695                 700

Ala Phe Cys Phe Ala Arg Trp Gly Gln Glu Pro Arg Asn Lys Cys Leu
705                 710                 715                 720

Pro Ala Gln Ala Ser Glu Phe Ser Pro Gln Arg Pro Phe Met Glu
                725                 730                 735

Ala Pro Cys Ser Pro Gly Pro Ala Leu Pro Trp Arg Leu Val Arg Arg
                740                 745                 750

Lys Arg Leu Leu Asp Val Leu Leu Leu Gly Ser Leu Leu Asn Gln Thr
            755                 760                 765

Ser Ile
770

<210> SEQ ID NO 6
<211> LENGTH: 2980
<212> TYPE: DNA
<213> ORGANISM: Mus musculus

<400> SEQUENCE: 6
ccgccgtaga ctgtgggtct gaaatctggt tgacgcagtc tgcggccact gctgagcttt        60
gggtaggcca ggctgggaa tcggccctgg atctctgctg tcgcatctcc ctacccaga         120 ctcctttcag catcaagtcc actatcctcg ccgtggccac gccctccgt atcctggctt        180 ctctgcgtcc tggctgttcc tccctgggtg gaggggagag gcagccatcc acttgcaggt       240
ggagcggggt ggagactctt cctgagccca gctgcaggac actgaggacc agcgagattc       300
ataggaccca attatggggt aagaggttt gcaggggttt gtgggagta cgtgcccaca         360 catatgtacc atagtcaata tccacgagct ggcagagcgt caccgaaaca agtaccctgg       420
atgtacgcct accatcgtgg tggacgccat gtgctgtctc cgatactggt acacagcaga       480
gtcgtgggtc tgcggcggcc agtggagaga atactactgt gctttgagaa atttgtttgc      540
agccttcacc tctgccggca tcaagttgat attcttcttt gatggcatgg tggagccggg       600
gaagcgagat gagtgggtaa agcgtagact caaaaacaac cggagagatat ccaagatttt      660 tcactacatc aagtcaaaaa gagaccagcc aggcagaaac atgttcttca ttccctctgg       720
gctggccata ttcacacggt tcgccctgaa gacactgggc caggagactt tctgttcatt       780
acaggaggca gactacgagg tggcttctta tggcctccag cacaactgtc tggggatcct       840
tggggaagac actgactact taattatga cacttgcccc tacttttcaa ttggcgatct       900
ctgcctagag agtctccaaa ccatcatgct ctgtcgagag aagctctgtg agagcctggg       960
cctccgtgtg gcagacccttc ctcttctggc ctgtctgctt ggcaatgaca tcactccaga     1020
gagcatgttt gaaagctttc ggtacaagtg cttgtcatcc tatgcttctg tgaaagagaa      1080
tgctggcaaa aaaggaaata ttatcctagc tgtctcagac tatatctcca agttcttca       1140 tttgtatcaa ggtgagaaga agatagaaga gatgctaccc ttggggccaa acaaagctct      1200
```

```
ctttttataaa ggagtaacct catatcttttt gccagggcag aaatctccat ggttagttca   1260
aaaacccaaa ggcatgataa cagacaaaca gcaaatggtg agtttaaatc ccgaatccaa   1320
gcaagaagtc cctatgtgta ttgatcctga attcaagcaa aagttcctg tgtgcactaa   1380 tcccgagtcc atgcaagaag ttcccatgtg tatggatcct gagcccaacc aggaagcttc   1440
catgtgcaca gatcccgaat ccaaacaaga agttcccatg tgcacagact ccgaatccaa   1500
gccagaagtt tcccaatata caaacccaga gagcaagcaa aaattacctt caggaataga   1560
cactgaattt aacctagaag cactcatgtg tacacaccct gaatttaaac aagaagatgt   1620
catggatatg gaacctgaaa taaagcaagt aaccatggtt tccgagtctg agatcttaaa   1680
ggttgccagg atgcatcacg tccactcaga aagctaccta gtgtacaaca ttctgagcag   1740
tggggagata gaatgcagta acaccctgga ggatgagctg gaccaagccc tcccgagcca   1800
agcctttatc taccgcccag tccggcagcg cgtctacgca ctcctactcg gggactggaa   1860
agatggagcc agcactggcc cagtggtcaa ggagtggttt gtgtacccg gtaactccct   1920 gaagcaccca gacctagtta ggcctctgca gatgaccgtt caaggggaa cacctagctt   1980 ggaagttctg tggctgagcc aagagccagc agtgcaggcc cagcgcctgg acaccttgct   2040
agcctgcttc aacctttcct cctcaagaga agagctgcaa gcagttgaga gcccgttgag   2100
agcgctgtgc tgcctcctga tctacctctt tgtccaggtg acactctttt ccctggaaga   2160
tctgcatgca tttatcgctc aggccttgtg cctccaagga aaatcaacct cccagctcat   2220
gcacttacag ctggattaca ttaactccag agctgtgcag ctgggatccc tcctcgtccg   2280
tggcctcacc acattggtac tagtcaatag cgcatgtggc ttcccctgga caacaagtga   2340
gtttatgccc tggaatgtgt ttgatggcaa gcttttccat cagaagtacc tgcagtctga   2400
aaagggatat gccgtggaag ttctttttga acaaaataga tcgtggctca ccaagttcca   2460
caacctgaag gcagtggtct gcaaggcctg ctccaaggag aaccggcgca tcgtaggcag   2520
aacgcattgg gactctcctt acacaggag gcaagggaga cagggctaca gctcctacag   2580
gacagactcc acacatggcc attctgggca gtcatgagaa aaccagggtt caggggcag   2640 acagcatgag cgtaaccact ggagaagata ctagatgctg tacagaagag tgtggaaaca   2700
ggatcaatgt ccagactctg ccctccggtc tcagcaacaa ggacagcaac tggggcaacc   2760
ctttaaagga aggaaaattg ctttttcagag gttttctccta cacaaactat aaaaatatcc   2820 cattggttg tttcagaggt tgctcctgac tccatgatcc agaacacttg acactatcat   2880
tgagaatgct ctcctgacct tagcaggagt ctaactccaa acattttctt actattaaat   2940
tgtgaaaatg tttcctcaaa aataaaaaa aaaaaaaaaa                          2980

<210> SEQ ID NO 7
<211> LENGTH: 3236
<212> TYPE: DNA
<213> ORGANISM: Homo sapiens

<400> SEQUENCE: 7
cgtcccgagc ggaagcgcct tgagcggaag cggaagtgaa cgaggcggct gtggcggtgg     60
ctgaggcggc tgggcctagg gtgcagcggg cgcgtctgcg gctggtgttg gcgcatctct    120
agatcctttc ccggagttca gttatgggtg tgagaggttt gcaaggattt gtgggaagta    180
cctgcccaca tatatgtaca gtagtaaatt tcaaagaact ggcagagcac caccgaagca    240
agtatcctgg atgtacccct accattgtgg ttgatgccat gtgttgtctc agatattggt    300
atactccaga atcttggatc tgcggtggcc agtggcgaga atacttttct gctttgcgag    360
```

```
attttgttaa aacttttacg gcagctggga tcaagttgat attcttcttt gatggcatgg    420
tggagcagga taagagagat gaatgggtga aacgaaggct caagaacaac agggagatat    480
ccaggatttt tcattacatc aagtcacaca aggagcagcc aggcagaaat atgttcttca    540
tcccctcagg gctagctgtg tttacacgat ttgctctaaa gacactgggc caggaaactt    600
tgtgttcttt gcaggaagca gattatgagg tagcttccta tggcctccag cataactgtc    660
ttgggattct gggggaagac actgattacc taatctatga cacttgtccc tacttttcaa    720
ttagcgagct ctgcctagag agcctggaca ccgtcatgct ctgcagagag aagctctgtg    780
agagtctggg cctctgtgtg gccgaccttc ctcttctggc ctgcctcctt ggcaacgaca    840
taatcccaga gggcatgttt gaaagcttta ggtacaaatg cttatcgtcc tacacctctg    900
taaaagagaa ctttgacaaa aaaggtaaca tcatattagc tgtgtcagac catatatcga    960
aagttcttta cttgtatcaa ggtgagaaaa aattagaaga gatattacct ctgggaccaa    1020
acaaagctct tttttataaa ggaatggcat catatctttt accaggacaa aaatctccat    1080 ggttttttcca aaaacccaaa ggtgtaataa cttggacaa acaagtaata tccacgagtt    1140
cagacgccga atccagggaa gaagttccca tgtgttcaga tgctgaatcc aggcaagaag    1200
ttcccatgtg tacaggccct gaatccaggc gagaagttcc cgtgtataca gattctgaac    1260
ccaggcaaga agttcccatg tgttcagacc ctgaacccag gcaagaagtt cccacatgta    1320
caggccctga atccaggcga agttcccca tgtgttcaga ccctgaaccc aggcaagaag    1380
ttcccatgtg tacaggccct gaagccaggc aagaagttcc catgtataca gactctgaac    1440
ccaggcaaga agttcccatg tatacagact ctgaacccag gcaagaagtt cccatgtata    1500
caggctctga acccaggcaa gaagttccca tgtatacagg ccctgaatcc aggcaagaag    1560
ttcccatgta tacaggccct gaatccaggc aagaagtttt aatacggaca gaccctgaat    1620
ctaggcaaga aattatgtgt acaggccatg aatccaaaca ggaagttccc atatgtacag    1680
atcctatatc caagcaagaa gactccatgt gtacacacgc tgaaatcaat caaaaattac    1740
ctgtagcaac agattttgaa tttaagctag aagctctcat gtgtacaaac cctgaaatta    1800
aacaagaaga ccccacaaat gtggggcctg aagtaaagca caagtaacc atggtttcag    1860 acactgaaat cttaaaggtt gctagaacac atcacgtcca agcagaaagc tacctggtgt    1920
acaacatcat gagcagtgga gagattgaat gcagcaacac cctagaagat gagcttgacc    1980
aggccttacc cagccaggcc ttcatttacc gtcccattcg acagcgggtc tactcactct    2040
tactggagga ctgtcaagat gtcaccagca cctgcctagc tgtcaaggag tggtttgtgt    2100
atcctgggaa cccactgagg cacccggacc tcgtcaggcc gctgcagatg accattccag    2160
ggggaacgcc tagtttgaaa atattatggc tgaaccaaga gccagaaata caggttcggc    2220
gcttggacac actcctagcc tgtttcaatc tttcctcctc aagagaagag ctgcaggctg    2280
tcgaaagccc atttcaagct ttgtgctgcc tcttgatcta cctctttgtc caggtggaca    2340
cgctttgcct ggaggatttg catgcgttta ttgcgcaggc cttgtgcctc caaggaaaat    2400
ccacctcgca gcttgtaaat ctacagcctg attacatcaa ccccagagcc gtgcagctgg    2460
gctcccttct cgtccgcggc ctcaccactc tggttttagt caacagcgca tgtggcttcc    2520
cctggaagac gagtgatttc atgccctgga atgtatttga cgggaagctt tttcatcaga    2580
agtacttgca atctgaaaag ggttatgctg tggaggttct tttagaacaa aatagatctc    2640
ggctcaccaa attccacaac ctgaaggcag tcgtctgcaa ggcctgcatg aaggagaaca    2700
gacgcatcac tggccgagcc cactgggget cacaccacgc agggaggtgg ggaagacagg    2760
```

-continued

| | |
|---|---|
| gctccagcta ccacaggacg ggctctgggt atagccgttc cagtcaggga cagccgtgga | 2820 |
| gagaccaggg accaggaagc agacagtatg agcatgacca gtggagaagg tactagtcaa | 2880 |
| cctccagaaa gagtatggag agaaaaagag gcacacctgg acgcagagcc ctgccagcgc | 2940 |
| cctcctctgc tgttgcagct gcaaggagac catgcctgtg ggagccaggc ctcgcttgca | 3000 |
| tgaagaagga acgatgcctt tttcaatggt gtctccctcc cattgtgcag aagagctttt | 3060 |
| gttggcttct ctcccgagct tgtgcctgat tctgtggccc aaaacaatca ttgttaacat | 3120 |
| cttcatgtgt ttcattctga tctttcattc atatatatga tgcctagcta atttcatttt | 3180 |
| aaaataaatg ggaatctgtt gtaaaaaaaa aaaaaaaaaa aaaaaaaaaa aaaaaa | 3236 |

<210> SEQ ID NO 8
<211> LENGTH: 4447
<212> TYPE: DNA
<213> ORGANISM: Rattus norvegicus

<400> SEQUENCE: 8

| | |
|---|---|
| atgggtgtaa gaggtttgca ggggtttgtg ggaagtacct gcccacatat atgtacaaca | 60 |
| gtcaatctcc acgagctggc agagagtcac cgagccaagt accctggaag tacgcccacc | 120 |
| attgtggtgg acgccatgtg ctgtctccga tactggtaca cagcagagtc ctgggtgtgc | 180 |
| ggcggccagt ggagagaata ctattcggct tgagagact tcctcgcggc cttcacatct | 240 |
| gctggcatca agctgatctt tttctttgac ggcacggtgg agccgggcaa gcgagacgag | 300 |
| tgggtaaagc gaagacttaa aaacaacagg gagatatcca ggatcttcca ctatatcaag | 360 |
| tcaaaaagag agcagccagg caggaacatg ttcttcatcc cctccggtct ggccatattc | 420 |
| acgcggttcg ccctgaagtc gttgggccag gagactttct gctcattgca ggaggcagac | 480 |
| tacgaggtgg cttcttatgg cctgcagcac aactgccttg ggatccttgg ggaagacact | 540 |
| gactacttaa tttatgacac ttgccccctac ttgtcaattg gtgacctctg tctggagagt | 600 |
| ctccaaacca tcctgctgtg tcgagagaag ctctgtgaga gcctgggcct ccgtgtgtca | 660 |
| gacctccctc tgctggcctg tctacttggc aatgacatca ctccagaggg catgttcgaa | 720 |
| agctttcggt acaagtgctt gtcatcctat gcttctgtga agagaatgc aggcaaaaaa | 780 |
| ggaaatatta tcctagccgt ctccgactat atctccaaag ttcttcattt gtatcaaggt | 840 |
| gagaagaaga tcgaagagat gctacccttg gggccaaaca aagctctctt ttataaagga | 900 |
| gtaacatcgt acctttttgcc agggcagaaa tctccatggt tagttcaaaa acccaaaagc | 960 |
| ataataacag acaagcaaat ggcgagttta accccggat ccaagcaaga agtccccatg | 1020 |
| tgcatagatc ctgaattcaa gcaagaagtt cctgtgtgca ctaatcccga gtccatgcaa | 1080 |
| gaagttccca tgtgtatgga ccctgaaccc aaccaggaag cttccgtgtg catggatcgc | 1140 |
| gaatccaagc cagaggttcc catgtgcact gatcctgaat ccaagccaga ggttcccctg | 1200 |
| tatacaaacc cagagagcaa gcaaaagtca ccttcagaaa tagaccccaa gtgcaatcta | 1260 |
| gaagcactca cgtgtacata ccctgaagtt aaacaagaag atgccatgga tatggaaccg | 1320 |
| gaaataaagc aagcaaccat ggtttcagag tctgaaatct taaaggttgc caggatgcat | 1380 |
| catgtccact cagaaagcta cctagtgtac aacattttga gcagtggaga gatagagtgt | 1440 |
| agtaacaccc tggaggacga gctggaccaa gccctcccaa gccaagcctt catctaccgc | 1500 |
| ccagtccggc agcgggtcta ctcactctta ctggaggact ggaaagacgg agccagcact | 1560 |
| ggtccagtgg tcaaggagtg gtttgtgtac cctggtaact ccctgaagca cccagaccta | 1620 |
| gtcaggcctc tgcagatgac cgttcaaggg ggaacgccta gcttggaagt tttgtggctg | 1680 |

```
agccaagagc cagcagccca ggcccggcgc ctggacacat tgctagcctg cttcaacctt   1740
tcctcctcaa gagaagagct gcaatccgtg gagagcccgt tgagggcgct gtgctgcctc   1800
ttgatctacc tgtttgtcca ggtggacact cttccctgg aagatctgca tgcatttatc    1860
gctcaggcct tgtgcctcca aggaaaatca acctcccagc ttatgcactt acagctggat   1920
tacatcaact ccagagctgt gcagctgggg tccctccttg tccgtggcct caccacattg   1980
gtactagtca acagtgcatg tggcttccct tggacaacca gcgactttat gccctggaat   2040
gtatttgacg gcaagctttt ccatcagaag tacctgcagt ctgaaaaagg atatggcgtg   2100
gagactcttt tggaacaaaa tagatcgtgg ctcaccacgt tccacaacct gaaggcagtg   2160
gtctgcaagg cctgctccaa ggagaaccga cgaattgtag gcaggataca ttggaactct   2220
cattacacag ggaggcaggg gagacagggc cacggctcct acagatcagg ctccacacat   2280
ggccattctg ggcagtcatg gagagaccag ggttcaggag gcagacagca tgagcatgac   2340
cactggagaa gatactaggt gctgtacagg taaagtcctc cccagcccct cagtgaacca   2400
gcagatgctc tgtcttcata gctgagggcc aaatagttaa tgtgtctcgt gggccagctt   2460
cccaaccggg atccaccgac ttgtttcaag ctgtgtctgc ttcttccaga agagtgtggg   2520
aaaaggttca acgccgggac tccgccctcc ttcaaggagt gtttagagtg gcatcaccca   2580
gtctcatcag agggacagta actgggacca cactttaaag gaaggaaaga ttgcttttca   2640
gtggattctc ctgcacatac tgtaaaaaga tcccatcggt ttgtttcaga cgttgctcct   2700
gactcccatg acccagaaca cgagacacta acgtcaagaa tgctcttctg accttagcag   2760
gagtctaatt ccaaacattt gctgactatt aaattgtgaa aatgtttcct caaatcattg   2820
gtctttgaaa tcatgatgtc ttcttatttt tctgttattg tgaaaaggaa ccatgaccaa   2880
agcgacttac aaaagaaagc atttaattta ggtcttaggt tccagaggg tggtagagcc     2940
tatggccatc gtgttgggc tagccaactg agaatggctc agggttttga aactttaaag    3000
cccaccccc cccccagcaa cacacctcca tcagcaaagc cacgcccct ccagtaaggc     3060
cacgcctcct aacccttcc accaaccaga gaccaagctt tcagacatac tagcttatgg    3120
ggctattctc attcagacca ccatacataa tatctaatag ctatatgatc agtcagaaat   3180
tacttttca ttagaaaaat ctagcagaaa taagcattca tctgtttttt ctttttttt     3240
tttttttt ttttggttct ttttttttc ggagctgggg accgaaccca gggccttggg      3300
cttcctaggc aagcgctcta ctactgagct aaatccccaa ccccctgttt ttttcttga    3360
tccacaaagt atttggatag gaaaaaaaaa acctaaattc ttgctttctt gtgggagagt   3420
tggttctgat tagaggaatg atggctcagt ggttaagaac agtggcagct cttccagaga   3480
cccaaggtct gatccccatc acccacacg tggctcacaa ctgtaactcc agttccaggg    3540
caatcgaaag cctcttctgg tctctgtgag cactaagcac acagtgatgc ccagacatgc   3600
atacaggaaa acaccccta aagatgaaat acatgttaaa aaaaaagat ttttaaagaa     3660
gcagagtggg ttacagtaag atcttcttta aactctgagg ttcttatcca tctccactgg   3720
ggaaacaaga gtagctgagc ctgtccaggg cccttacagc cctgctctat ctctagggac   3780
acgcagttcc ctgaggagat gcaagctcac tggaagatgt gtccttttcg tgctccggtc   3840
tttaagattt tgataagctt ctaaaatgtt ccttgtcgtc tttacagttt tgcagaccac   3900
tggctcagcc atgctgtagg agctcttggg tttctccttg agattcttgt gtttaccaga   3960
agggtacagc cccatctccc gcatttgagc atgcttgtgt tgttcagcc cctttctgct    4020
cccggaggac tgagcatagt gtgtccggag agcttgtact gctatgtctg ctgcctagac   4080
```

```
taggaactgg cttttctggt ccttcccttg aacaccgtct tcttcctgtc tgctactctc    4140
tgacatcgct gcctttagga gttctgtttc cttgctgttt acctgtgtga ctgtgaatta    4200
agattctgat ctcttagact gaaagtatat ttccgtgaaa gttgttttcc gtcacagaag    4260
ctgcatcctg acttgtcaat aaagtgtgta tgtcagtcac atttaaataa gtttaaataa    4320
gccactgtgt tgatggaata ttaatcacat ttagaacttt tccggggaca gcattgtttt    4380
ccagtcaagt cttgtgatag aatttccaca tatcaattta aaataaaaat acattttaa     4440 actcata                                                              4447
```

<210> SEQ ID NO 9
<211> LENGTH: 1375
<212> TYPE: DNA
<213> ORGANISM: Canis lupus

<400> SEQUENCE: 9

```
cacggtccgg ggagatccgc ggcggcggcg gcggcggcgg ccggacttag cactcaggac      60
cgtgaggcag gagattcgaa gacttccaaa gaaggaccag ttcctcggat gagccccctt     120
acagagagat gaaggggcag cagaaaacag ctgaaacgga gaggggacag tgcagattc      180 aggaaggtgc agtggcaact ggggaggacc caaccagtgt ggctattgcc agcatccaat     240
cagctgccac tttccctgac cccaacgtca agtacgtctt ccgaactgag aatgggggcc     300
aggtgatgta cagggtgatc caggtgtctg aggggcagct ggatggccag actgagggga     360
ctggcgccat cagtggctat cctgccactc aatccatgac ccaggccgtg atccaggtg      420 cgttcaccag tgacgatgca gttgacacag aggggacggc cgccgaaacg cactatactt     480
acttccccag cactgcagtg ggagatgggg caggggggac cacgtcgggg agacagttct     540
ttgtgatgat gtcgccacag gaagtgttgc agggaggaag ccagcgctcc attgccccca     600
ggactcaccc ttattcccg aagtcagaag ctcccaggac gactcgggat gagaaacgca      660
gggctcagca taatgaagtt gaacgccgcc gccgagacaa gattaacaac tggattgtgc     720
agctgtccaa gatcatccca gactgctcca tggagagcac caagtctggc cagagtaaag     780
gtgggattct gtccaaagcc tgtgattata tccaggagct tcgacagagt aaccaccggt     840
tgtctgaaga actgcagggg ctcgaccaac tgcagctgga caacgatgtg ctccgacagc     900
aggtggaaga tcttaaaaac aagaacctgc tgctacgggc tcagctgcgg cacccacggag    960 tagaggtcgt catcaagaat gacagcaact aactgtgggg actcgagggc cttaggccct    1020
acagccccct tccaagaact gcagatagtc caggagaacg gctcacccgt gccccttccc    1080
ttcaccaccc acttctggcg tgggaccagg gggagctcag aaagcatggc tttgaactga    1140
ggcccggtga cagcagcgtg cagtggtgtg aaacacacgt gggtgtgcgc tgacagcctc    1200
gtccagtccc accgcgcggc ccctgagccc tcgtgtccct cttcacatgc atgtgccgtc    1260
tccatgctgg ataccggaca caacgtgggg gcttgccctg tgcttgcttc gagaaccagc    1320
agagggtctg ctgacaagtg acgctctggt tgccccagga ctctggcgct cccac         1375
```

<210> SEQ ID NO 10
<211> LENGTH: 2313
<212> TYPE: DNA
<213> ORGANISM: Bos taurus

<400> SEQUENCE: 10

```
atggccgagt ctgtgggtgg gagaggcggc cgcctggagc ctgccacct gcgcgcctcc        60 ttgcgggctt ggcggctggg tcctcaggcc ccacatggcc gaggaagaag ccggtctcct     120
```

```
ttcacagcag agaaagagtc agactcccgc tggatccttc ccaggagttc cattatgggt    180
gtgagaggtt tgcatgggtt tgtggcaagt agctgcccac atgtatgtac ggtagtaaac    240
ttcaaggagc tggcagagcg ccaccggagc cagcaccccg gagggacgcc caccattgtg    300
gtcgacgcca tgtgctgcct caggtactgg tacacaccgg agtcctgggt ctgcggcgga    360
cagtggcggg aatactattc ttcttttgcga gaattcgtga gaacttttac cgctgttggc    420
atcaagctga tcttcttctt cgatggcatg gtggagcagt ccaagagaga cgagtgggtg    480
aaacgcagac tcaagaataa cagggagata gccaagatct ccactacat caagtcccgc    540
agggagcagc cgggcagaaa catgttcttc atccctcgg ggctggccat atttacgcgg    600
tttgctttga aggccctggg tcaggaaact ctgtgctcgt tacaggaggc cgactatgag    660
gtggcctcct atggcttcca gaacaactgt cttgggattc ttggagaaga cactgactac    720
ttaatctatg acacctgtcc ctattttcc atcagcgagc tctccctgga cagtctggac    780
accgtcatgc tctgccggga gaagctctgt cagagcctcg ggctccacct ggccgacctg    840
cctctgctgg cctgcctgct tggcaatgac gtcatcccag aaggcatgtt cgagagcttt    900
cggtacaaat gcttgacttc ctatgcctct gtgagagaga gctgtgacag aaaaggtaac    960
gttatcttag ctgtagcaga gcacatatct aaagttcttc ggttgcatca aggtgagaaa   1020
aagctggaag atgctacc tttgggacca aacaaagctc ttttttataa aggagtagcg   1080
tcgtatcttt tgccaggaca gaaatctcca tggtttatcc aaaaacctga agatgtagta   1140
actttggaca gcaggtact atccatgagt tcagatcctg aatctaagca agagtttccc   1200
gtgtgtatgg actctgaatc caagcagaaa ttacctgtgg gtacagaccc tgaatttaac   1260
ctagaagcac ccatgtgtac aaacactgaa gttaaacaag aagaccctgt aaatgtgggg   1320
cctgaagcca agcatcaagt aactgtggtt ttggatcctg aaatcttaaa ggtaggtgga   1380
catgcccacc cgaatacgac acagagcctt gatggagggt tggaggcgga cctgcacgtg   1440
gaggtcccga cgagcatgca gcccgaggag aaaggtgagc agaggcagga caggggccc   1500
agtctgcgct tggcttccat gcttagtgtg actcacgtcc atcgagtcag tgatgccatc   1560
cagccatctc atcctctaaa caagttgcat ttaattgttg ggcaggtcgc cagagcacag   1620
catgtccagg cagagagcta cctggtgtac agcgtgatga gcagcggcga ggtggagtgc   1680
agcaacagct ggaggacgc cacggaccag gccctgccca gccaggcctt cgtctaccgc   1740
cccgtgcggc agcgcgtcta ctcccttctg ctgggggggcg gcggcggtgg ttccagcacc   1800
ggccccgctg tcaaggagtg gttttgtgtac tccgggaacc cactgaggca gccggacctc   1860
gtcaggccgc tgcagatgaa cattccaggg ggaacgccta gtttgagaca gctgtggctg   1920
agccaagagc caggaatcca ggcccagcgc ttggacacac tgctggcctg ctttgacctg   1980
tcatcctcac gagaagaact gcaggcagtt gagcgcccct tcaggcgtt gtgctgcctc   2040
ctggtctacc tgttcgtgca ggtgaagcat aaaagtgacc ttggatggga acagaccgcg   2100
cagaggagag ctgcttttg ttttgctcgc tgggggcagg agccgcgtaa caagtgcttg   2160
cccgcccagg cctcggagtt ctcaccacag cgtcggccct tcatggaggc gccgctcg   2220
ccaggcccag ccctgccctg gcgccttgtg aggaggaaga gacttctgga tgtgctcctg   2280
ctgggctcct tgttaaacca aacctcgatc tga                                2313
```

<210> SEQ ID NO 11
<211> LENGTH: 50
<212> TYPE: DNA
<213> ORGANISM: Mus musculus

```
<400> SEQUENCE: 11
caccgcaaat ggtgagttta atcccgaag gatttaaact caccatttgc        50

<210> SEQ ID NO 12
<211> LENGTH: 50
<212> TYPE: DNA
<213> ORGANISM: Mus musculus

<400> SEQUENCE: 12
caccgcccac acatatgtac catagcgaac tatggtacat atgtgtgggc        50

<210> SEQ ID NO 13
<211> LENGTH: 15
<212> TYPE: PRT
<213> ORGANISM: Mus musculus

<400> SEQUENCE: 13

Gly Ile Leu Gly Glu Asp Thr Asp Tyr Leu Ile Tyr Asp Thr Cys
1               5                   10                  15

<210> SEQ ID NO 14
<211> LENGTH: 25
<212> TYPE: DNA
<213> ORGANISM: Mus musculus
<220> FEATURE:
<221> NAME/KEY: misc_feature
<222> LOCATION: (1)..(1)
<223> OTHER INFORMATION: forward primer

<400> SEQUENCE: 14
gaagcactca tgtgtacaca ccctg                                   25

<210> SEQ ID NO 15
<211> LENGTH: 23
<212> TYPE: DNA
<213> ORGANISM: Mus musculus
<220> FEATURE:
<221> NAME/KEY: misc_feature
<222> LOCATION: (1)..(1)
<223> OTHER INFORMATION: reverse primer

<400> SEQUENCE: 15
ccactccttg accactgggc cag                                     23

<210> SEQ ID NO 16
<211> LENGTH: 50
<212> TYPE: DNA
<213> ORGANISM: Mus musculus

<400> SEQUENCE: 16
caccgcttag agataacaac catagcgaac tatggttgtt atctctaagc        50

<210> SEQ ID NO 17
<211> LENGTH: 25
<212> TYPE: DNA
<213> ORGANISM: Mus musculus

<400> SEQUENCE: 17
gagacagcac atggcgtcca ccacg                                   25

<210> SEQ ID NO 18
<211> LENGTH: 38
<212> TYPE: DNA
<213> ORGANISM: Mus musculus

<400> SEQUENCE: 18
```

```
gaccacgcgt atcgatgtcg acttttttttt tttttttt                         38

<210> SEQ ID NO 19
<211> LENGTH: 23
<212> TYPE: DNA
<213> ORGANISM: Mus musculus

<400> SEQUENCE: 19
ggtgacgctc tgccagctcg tgg                                          23

<210> SEQ ID NO 20
<211> LENGTH: 18
<212> TYPE: DNA
<213> ORGANISM: Mus musculus

<400> SEQUENCE: 20
gaccacgcgt atcgatgt                                                18

<210> SEQ ID NO 21
<211> LENGTH: 24
<212> TYPE: DNA
<213> ORGANISM: Mus musculus

<400> SEQUENCE: 21
cgtaggcaga acgcattggg actc                                         24
```